United States Patent
Ruoslahti et al.

(10) Patent No.: US 9,522,198 B2
(45) Date of Patent: Dec. 20, 2016

(54) METHODS AND COMPOSITIONS RELATED TO TARGETING TUMORS AND WOUNDS

(71) Applicant: Sanford-Burnham Medical Research Institute, La Jolla, CA (US)

(72) Inventors: Erkki Ruoslahti, Buelton, CA (US); Jan Pilch, Pittsburgh, PA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 74 days.

(21) Appl. No.: 14/331,048

(22) Filed: Jul. 14, 2014

(65) Prior Publication Data

US 2014/0377184 A1 Dec. 25, 2014

Related U.S. Application Data

(63) Continuation of application No. 12/162,751, filed as application No. PCT/US2007/003156 on Feb. 5, 2007, now Pat. No. 8,815,804.

(60) Provisional application No. 60/765,540, filed on Feb. 6, 2006.

(51) Int. Cl.

| | |
|---|---|
| C07K 7/00 | (2006.01) |
| C07K 7/06 | (2006.01) |
| C07K 7/64 | (2006.01) |
| C07K 14/00 | (2006.01) |
| C07K 19/00 | (2006.01) |
| A61K 38/04 | (2006.01) |
| A61K 38/08 | (2006.01) |
| A61K 38/16 | (2006.01) |
| A61K 38/17 | (2006.01) |
| A61K 49/00 | (2006.01) |
| A61K 47/48 | (2006.01) |
| A61K 49/08 | (2006.01) |
| A61K 49/14 | (2006.01) |
| A61K 38/12 | (2006.01) |
| A61K 38/10 | (2006.01) |

(52) U.S. Cl.
CPC ........ *A61K 49/0056* (2013.01); *A61K 38/08* (2013.01); *A61K 47/48246* (2013.01); *A61K 49/0043* (2013.01); *A61K 49/085* (2013.01); *A61K 49/14* (2013.01); *C07K 7/06* (2013.01); *A61K 38/10* (2013.01); *A61K 38/12* (2013.01); *A61K 38/16* (2013.01); *A61K 38/17* (2013.01); *C07K 7/64* (2013.01); *C07K 14/00* (2013.01); *C07K 2319/00* (2013.01); *C07K 2319/01* (2013.01); *C07K 2319/035* (2013.01)

(58) Field of Classification Search
CPC ........ A61K 38/08; A61K 38/04; A61K 38/10; A61K 38/12; A61K 38/16; A61K 38/17; C07K 7/06; C07K 7/64; C07K 14/00; C07K 2319/00; C07K 2319/01; C07K 2319/035
See application file for complete search history.

(56) References Cited

U.S. PATENT DOCUMENTS

| | | |
|---|---|---|
| 3,610,795 A | 10/1971 | Antoine et al. |
| 5,011,686 A | 4/1991 | Pang |
| 5,622,699 A | 4/1997 | Ruoslahti et al. |
| 5,789,542 A | 8/1998 | McLaughlin et al. |
| 5,792,742 A | 8/1998 | Gold et al. |
| 6,537,520 B1 | 3/2003 | Rajopadhye et al. |
| 6,984,373 B2 | 1/2006 | Wescott et al. |
| 7,041,790 B2 | 5/2006 | Wescott et al. |
| 7,413,727 B2 | 8/2008 | Klaveness et al. |

FOREIGN PATENT DOCUMENTS

| | | |
|---|---|---|
| WO | 01/09188 A1 | 2/2001 |
| WO | 02/055544 A2 | 7/2002 |
| WO | 2003/083436 A2 | 10/2003 |

OTHER PUBLICATIONS

Abe, K. et al., "Regulation of vascular endothelial growth factor production and angiogenesis by the cytoplasmic tail of tissue factor", Proc Natl Acad Sci. 96(15), 1999, 8663-8.
Akerman, M.E. et al., "Nanocrystal targeting in vivo", Proc Natl Acad Sci. 99(20), 2002, 12617-21.
Allam, M. et al., "Cholera toxin triggers apoptosis in human lung cancer cell lines", Cancer Res. 57(13), 1997, 2615-8.
Alvarez-Bravo, J. et al., "Novel synthetic antimicrobial peptides effective against methicillin-resistant *Staphylococcus aureus*", Biochem J. 302 (Pt 2), 1994, 535-8.
Askew, B. et al., "Molecular recognition with convergent functional groups. VI. Synthetic and structural studies with a model receptor for nucleic acid components", J. Am. Chem. Soc. 111(3), 1989, 1082-1090.
Aukerman, M.J. et al., "An arginine to lysine substitution in the bZIP domain of an opaque-2 mutant in maize abolishes specific DNA binding", Genes Dev. 5(2), 1991, 310-20.
Baneyx, G. et al., "Coexisting conformations of fibronectin in cell culture imaged using fluorescence resonance energy transfer", Proc Natl Acad Sci. 98(25), 2001, 14464-8.
Bessalle, R. et al., "All-D-magainin: chirality, antimicrobial activity and proteolytic resistance", FEBS Lett. 274(1-2), 1990, 151-5.
Bissell, M.J. et al., "Putting tumours in context", Nat Rev Cancer. 1(1), 2001, 46-54.
Blondelle, S.E. et al., "Design of model amphipathic peptides having potent antimicrobial activities", Biochemistry 31(50), 1992, 12688-94.
Blondelle, S.E. et al., "Progress in Antimicrobial Peptides", Annual Reports in Medicinal Chemistry, 27, 1992, 159-168.

(Continued)

*Primary Examiner* — Bridget E Bunner
(74) *Attorney, Agent, or Firm* — Krista P. Kauppinen

(57) ABSTRACT

Disclosed are compositions and methods useful for targeting tumors, sites of injury and blood clots. The compositions and methods are based on peptide sequences that selectively bind to and home to tumors, sties of injury and blood clots in animals. The disclosed targeting is useful for delivering therapeutic and detectable agents to tumors, sites of injury and blood clots.

21 Claims, 8 Drawing Sheets

(56) References Cited

OTHER PUBLICATIONS

Borgstrom, P. et al., "Importance of VEGF for breast cancer angiogenesis in vivo: implications from intravital microscopy of combination treatments with an anti-VEGF neutralizing monoclonal antibody and doxorubicin", Anticancer Res. 19, 1999, 4213-14.
Bork, P. et al., "Go hunting in sequence databases but watch out for the traps", Trends Genet. 12(10), 1996, 425-7.
Bork, P., "Powers and pitfalls in sequence analysis: the 70% hurdle", Genome Res. 10(4), 2000, 398-400.
Brenner, S.E. et al., "Errors in genome annotation", Trends Genet. 15(4), 1999, 132-3.
Chan, S. et al., "Prospective randomized trial of docetaxel versus doxorubicin in patients with metastatic breast cancer", J Clin Oncol. 17(8), 1999, 2341-54.
Crown, J.P., "The platinum agents: a role in breast cancer treatment?", Semin Oncol. 28(1 Suppl 3), 2001, 28-37.
Davis, S. et al., "Isolation of angiopoietin-1, a ligand for the TIE2 receptor, by secretion-trap expression cloning", Cell. 87(7), 1996, 1161-9.
Doerks, T. et al., "Protein annotation: detective work for function prediction", Trends Genet. 14(6), 998, 248-50.
Dvorak, H.F. et al., "Regulation of extravascular coagulation by microvascular permeability", Science. 227(4690), 1985, 1059-61.
Eichinger, L. et al., "The genome of the social amoeba Dictyostelium discoideum", Nature. 435, 2005, 43-57.
Eichinger et al. Genbank Accession No. Q54WC0; May 24, 2005, 2 pages.
Ellerby, H.M. et al., "Anti-cancer activity of targeted pro-apoptotic peptides", Nat Med. 5(9), 1999, 1032-8.
Esteras-Chopo, A. et al., "The amyloid stretch hypothesis: recruiting proteins toward the dark side", Proc Natl Acad Sci. 102(46), 2005, 16672-7.
Fisher, B. et al., "Tamoxifen for prevention of breast cancer: report of the National Surgical Adjuvant Breast and Bowel Project P-1 Study", J Natl Cancer Inst. 90(18), 1998, 1371-88.
Flacke, S. et al., "Novel MRI contrast agent for molecular imaging of fibrin: implications for detecting vulnerable plaques", Circulation. 104(11), 2001, 1280-5.
Folkman, J. et al., "Addressing tumor blood vessels", Nat Biotechnol. 15(6), 1997, 510-519.
Folkman, J. et al., "Angiogenesis", J Biol Chem. 267(16), 1992, 10931-4.
Hagedorn, M. et al., "Target molecules for anti-angiogenic therapy: from basic research to clinical trials", Crit Rev Oncol Hematol. 34(2), 2000, 89-110.
Halin, C. et al., "Enhancement of the antitumor activity of interleukin-12 by targeted delivery to neovasculature", Nat Biotechnol. 20(3), 2002, 264-9.
Hoffman, R.M. et al., "The multiple uses of fluorescent proteins to visualize cancer in vivo", Nat Rev Cancer. 5(10), 2005, 796-806.
Homandberg, G.A. et al., "Heparin-binding fragments of fibronectin are potent inhibitors of endothelial cell growth", Am J Pathol. 120(3), 1985, 327-32.
Homandberg, G.A. et al., "Heparin-binding fragments of fibronectin are potent inhibitors of endothelial cell growth: structure-function correlations", Biochim Biophys Acta. 874(1), 1986, 61-71.
Ivanova, N. et al., "Genome sequence of *Bacillus cereus* and comparative analysis with *Bacillus anthracis*", Nature. 423, 2003, 87-91.
Jaffer, F.A. et al., "Molecular imaging of factor XIIIa activity in thrombosis using a novel, near-infrared fluorescent contrast agent that covalently links to thrombi", Circulation. 110(2), 2004, 170-6.
Javadpour, M.M. et al., "De novo antimicrobial peptides with low mammalian cell toxicity", J Med Chem. 39(16), 1996, 3107-13.
Kalluri, R., "Basement membranes: structure, assembly and role in tumour angiogenesis", Nat Rev Cancer. 3(6), 2003, 422-33.
Kaneko, T. et al., "Structural analysis of Arabidopsis thaliana chromosome 3. II. Sequence features of the 4,251,694 by regions covered by 90 P1, TAC and BAC clones", DNA Res. 7(3), 2000, 217-21.
Kirsch, M. et al., "Anti-angiogenic treatment strategies for malignant brain tumors", J Neurooncol. 50(1-2), 2000, 149-63.
Knowles, L.M. et al., "CLT1 targets angiogenic endothelium through CLIC1 and fibronectin", Angiogenesis. 15(1), 2012, 115-29.
Komatsu, M. et al., "R-Ras is a global regulator of vascular regeneration that suppresses intimal hyperplasia and tumor angiogenesis", Nat Med. 11(12), 2005, 1346-50.
Kreitman, R.J. et al., "Recombinant toxins containing human granulocyte-macrophage colony-stimulating factor and either pseudomonas exotoxin or diphtheria toxin kill gastrointestinal cancer and leukemia cells", Blood. 90(1), 1997, 252-9.
Laakkonen, P. et al., "Antitumor activity of a homing peptide that targets tumor lymphatics and tumor cells", Proc Natl Acad Sci. 101(25), 2004, 9381-6.
Lewis, R.A. et al., "Automated site-directed drug design: the concept of spacer skeletons for primary structure generation", Proc R Soc Lond B Biol Sci. 236(1283), 1989, 125-40.
Lewis, R.A. et al., "Automated site-directed drug design: the formation of molecular templates in primary structure generation", Proc R Soc Lond B Biol Sci. 236(1283), 1989, 141-62.
Maloy, W.L. et al., "Structure-activity studies on magainins and other host defense peptides", Biopolymers. 37(2), 1995, 105-22.
Mancheno, J.M. et al., "A peptide of nine amino acid residues from alpha-sarcin cytotoxin is a membrane-perturbing structure", J Pept Res. 51(2), 1998, 142-8.
Martin, V. et al., "Cancer gene therapy by thyroid hormone-mediated expression of toxin genes", Cancer Res. 60(12), 2000, 3218-24.
McKinlay, M.A. et al., "Rational design of antiviral agents", Annu Rev Pharmacol Toxicol. 29, 1989, 111-22.
Morla, A. et al., "A fibronectin self-assembly site involved in fibronectin matrix assembly: reconstruction in a synthetic peptide", J Cell Biol. 118(2), 1992, 421-9.
Mosher, D.F. et al., "Cross-linking of cold-insoluble globulin by fibrin-stabilizing factor", J Biol Chem. 250(16), 1975, 6614-21.
Neri, D. et al., "Targeting by affinity-matured recombinant antibody fragments of an angiogenesis associated fibronectin isoform", Nat Biotechnol. 15(12), 1997, 1271-5.
Ngo, J.T. et al., "Computational Complexity, Protein Structure Prediction, and the Levinthal Paradox", The Protein Folding Problem and Tertiary Structure Prediction, Kenneth M. Merz Jr. and Scott M. Le Grand (Eds.), Birkhäuser Boston, 1994, 492-495.
O'Reilly, M.S. et al., "Angiostatin: a novel angiogenesis inhibitor that mediates the suppression of metastases by a Lewis lung carcinoma", Cell. 79(2), 1994, 315-28.
O'Reilly, M.S. et al., "Antiangiogenic activity of the cleaved conformation of the serpin antithrombin", Science. 285(5435), 1999, 1926-8.
O'Reilly, M.S. et al., "Endostatin: an endogenous inhibitor of angiogenesis and tumor growth", Cell. 88(2), 1997, 277-85.
Osborne, C.K. et al., "Targeting the epidermal growth factor receptor in breast cancer cell lines with a recombinant ligand fusion toxin (DAB389EGF)", Cancer J Sci Am. 2(3), 1996, 175-80.
Palumbo, J.S. et al., "Fibrinogen is an important determinant of the metastatic potential of circulating tumor cells", Blood 96(10), 2000, 3302-9.
Paridaens, R. et al., "Paclitaxel versus doxorubicin as first-line single-agent chemotherapy for metastatic breast cancer: a European Organization for Research and Treatment of Cancer Randomized Study with cross-over", J Clin Oncol. 18(4), 2000, 724-33.
Perry, N.C. et al., "The use of 3D modelling databases for identifying structure activity relationships", Prog Clin Biol Res. 291, 1989, 189-93.
Pilch, J. et al., "Peptides selected for binding to clotted plasma accumulate in tumor stroma and wounds", Proc Natl Acad Sci. 103(8), 2006, 2800-4.
Pilch, J. et al., "The anti-angiogenic peptide anginex disrupts the cell membrane", J Mol Biol. 356(4), 2006, 876-85.

(56) References Cited

OTHER PUBLICATIONS

Powers, W.J. et al., "Indium-111 platelet scintigraphy in cerebrovascular disease", Neurology. 32(9), 1982, 938-43.
Reith et al. Genbank Accession No. P51375; Oct. 1, 1996, 4 pages.
Ruoslahti, E., "Specialization of tumour vasculature", Nat Rev Cancer. 2002, 2(2), 2002, 83-90.
Saberwal, G. et al., "Cell-lytic and antibacterial peptides that act by perturbing the barrier function of membranes: facets of their conformational features, structure-function correlations and membrane-perturbing abilities", Biochim Biophys Acta. 1197(2), 1994, 109-31.
Sakai, T. et al., "Plasma fibronectin supports neuronal survival and reduces brain injury following transient focal cerebral ischemia but is not essential for skin-wound healing and hemostasis", Nat Med. 7(3), 2001, 324-30.
Schwartz et al., "Single amino acid substitutions in proteins of the armadillo gene family abolish their binding to alpha-catenin", J Biol Chem. 271(3), 1996, 1520-6.
Senger, D.R. et al., "Tumor cells secrete a vascular permeability factor that promotes accumulation of ascites fluid", Science. 219(4587), 1983, 983-5.
Siegel, P.M. et al., "Elevated expression of activated forms of Neu/ErbB-2 and ErbB-3 are involved in the induction of mammary tumors in transgenic mice: implications for human breast cancer", EMBO J. 18(8), 1999, 2149-64.
Skolnick, J. et al., "From genes to protein structure and function: novel applications of computational approaches in the genomic era", Trends Biotechnol. 18(1), 2000, 34-9.
Slavin, J. et al., "Fibroblast growth factors: at the heart of angiogenesis", Cell Biol Int. 19(5), 1995, 431-44.
Smith, T.F. et al., "The challenges of genome sequence annotation or 'the devil is in the details'", Nat Biotechnol. 15(12), 1997, 1222-3.
Song, L.L. et al., "Cancer stem cells—an old idea that's new again: implications for the diagnosis and treatment of breast cancer", Expert Opin Biol Ther. 7(4), 2007, 431-8.
St Croix, B. et al., "Genes expressed in human tumor endothelium", Science 289(5482), 2000, 1197-202.
Suh, T.T. et al., "Resolution of spontaneous bleeding events but failure of pregnancy in fibrinogen-deficient mice", Genes Dev. 9(16), 1995, 2020-33.
Suri, C. et al., "Requisite role of angiopoietin-1, a ligand for the TIE2 receptor, during embryonic angiogenesis", Cell 87(7), 1996 1171-80.
Tannock and Hill, "The Basic Science of Oncology," 1998, New York, McGraw-Hill, pp. 357-358.
ten Cate, H. et al., "The activation of factor X and prothrombin by recombinant factor VIIa in vivo is mediated by tissue factor", J Clin Invest. 92(3), 1993, 1207-12.
Thakur, M.L. et al., "Indium-LLL labeled platelets: studies on preparation and evaluation of in vitro and in vivo functions", Thromb Res. 9(4), 1976, 345-57.
Ventimiglia, J.B. et al., "Tenascin expression in human glioma cell lines and normal tissues", J Neuroimmunol. 36(1), 1992, 41-55.
Wells, J.A. et al., "Additivity of mutational effects in proteins", Biochemistry. 29(37), 1990, 8509-17.
White, C.A. et al., "Antibody-targeted immunotherapy for treatment of malignancy", Annu Rev Med. 52, 2001, 125-41.
Wieland, H.A. et al., "A single histidine in GABAA receptors is essential for benzodiazepine agonist binding", J Biol Chem. 267(3), 1992, 1426-9.
Yang, M. et al., "Whole-body optical imaging of green fluorescent protein-expressing tumors and metastases", Proc Natl Acad Sci. 97(3), 2000, 1206-11.
Yi, M. et al., "Antiangiogenic proteins require plasma fibronectin or vitronectin for in vivo activity", Proc Natl Acad Sci. 100(20), 2003, 1143-58.

METHODS AND COMPOSITIONS RELATED TO TARGETING TUMORS AND WOUNDS

CROSS-REFERENCE TO RELATED APPLICATIONS

This application is a continuation of U.S. patent application Ser. No. 12/162,751, filed on Jan. 23, 2009, now U.S. Pat. No. 8,815,804, which is a national stage filing of PCT/US07/03156, filed on Feb. 5, 2007, and which claims the benefit of U.S. provisional application No. 60/765,540, filed on Feb. 5, 2006, all of which are hereby incorporated by reference in their entirety.

STATEMENT REGARDING FEDERALLY SPONSORED RESEARCH

This invention was made with government support under Grant DAMD 17-02-1-0315 from the DoD, Contract NO1-CO-37007 from the NCI, and Grants CA099258 and CA103563 from the NIH. The government has certain rights in the invention.

FIELD OF THE INVENTION

The present invention relates generally to the fields of molecular medicine and cancer biology and, more specifically, to molecules that selectively home to tumor stroma and wound sites.

BACKGROUND OF THE INVENTION

A major hurdle to advances in treating cancer is the relative lack of agents that can selectively target the cancer while sparing normal tissue. For example, radiation therapy and surgery, which generally are localized treatments, can cause substantial damage to normal tissue in the treatment field, resulting in scarring and loss of normal tissue. Chemotherapy, in comparison, which generally is administered systemically, can cause substantial damage to organs such as the bone marrow, mucosae, skin and small intestine, which undergo rapid cell turnover and continuous cell division. As a result, undesirable side effects such as nausea, loss of hair and drop in blood cell count often occur when a cancer patient is treated intravenously with a chemotherapeutic drug. Such undesirable side effects can limit the amount of a drug that can be safely administered, thereby hampering survival rate and impacting the quality of patient life.

Regarding tissue injuries, substantive basic science and clinical research have been conducted to evaluate the mechanisms of wound healing, the efficacy of various modalities for treatment of wounds, and the best methods for diagnosing wound infection. A great deal of this effort has been directed toward evaluating the most accurate and reproducible methods for diagnosing chronic wound infection. Chronic wounds often harbor bacteria at levels many times that which constitute infection in an acute surgical wound; yet, many of these chronic wounds go on to closure despite very high levels of microorganisms. There are several intrinsic limitations to diagnosing a wound infection and establishing a treatment paradigm via clinical signs and symptoms alone. Of particular concern is the constantly evolving number of microorganisms with antibiotic resistance. While the evaluation of clinical signs and symptoms may prove to be a very cost-effective and expedient method for diagnosing chronic wound infection, the use of this method alone does not inform the wound care clinician of the most appropriate chemotherapeutic approach to treatment. Use of clinical signs and symptoms alone leaves the provider to select a therapeutic agent based on little specific information about the particular pathogen(s).

Thus, there is a need for new therapeutic strategies for selectively targeting tumors and wounds, and reducing the side effects associated with systemic therapy. The present invention satisfies this need by providing molecules that selectively home to tumors and tissue injuries, and which are suitable for selectively targeting chemotherapeutic drugs, gene therapy vectors or other agents to the appropriate tissue. Related advantages also are provided.

BRIEF SUMMARY OF THE INVENTION

Disclosed are methods and compositions related to an isolated peptide comprising an amino acid segment comprising the amino acid sequence of SEQ ID NO: 1 or SEQ ID NO: 2 or related amino acid sequences.

Also disclosed are methods of directing a moiety to tumors, sites of injury, and/or sites of blood clots in a subject, comprising administering to the subject a conjugate comprising a peptide comprising an amino acid segment comprising the amino acid sequence of SEQ ID NO: 1 or SEQ ID NO: 2 or related amino acid sequences.

Also disclosed are isolated peptides comprising an amino acid segment comprising the amino acid sequence of SEQ ID NO: 1 or SEQ ID NO: 2, an amino acid sequence at least about 90% identical to the amino acid sequence of SEQ ID NO:1 or SEQ ID NO:2, or the amino acid sequence of SEQ ID NO:1 or SEQ ID NO:2 having one or more conservative amino acid substitutions.

Also disclosed are conjugates, wherein the conjugate comprises a moiety linked to a peptide comprising an amino acid segment comprising the amino acid sequence of SEQ ID NO: 1 or SEQ ID NO: 2, an amino acid sequence at least about 90% identical to the amino acid sequence of SEQ ID NO:1 or SEQ ID NO:2, or the amino acid sequence of SEQ ID NO:1 or SEQ ID NO:2 having one or more conservative amino acid substitutions.

Also disclosed are methods of directing a moiety to tumors, sites of injury, and/or sites of blood clots in a subject, comprising administering to the subject a conjugate, wherein the conjugate comprises a moiety linked to a peptide comprising an amino acid segment comprising the amino acid sequence of SEQ ID NO: 1 or SEQ ID NO: 2, an amino acid sequence at least about 90% identical to the amino acid sequence of SEQ ID NO:1 or SEQ ID NO:2, or the amino acid sequence of SEQ ID NO:1 or SEQ ID NO:2 having one or more conservative amino acid substitutions.

The peptide can have a length of less than 100 residues. The peptide can have a length of less than 50 residues. The peptide can have a length of less than 20 residues. The amino acid segment can comprise an amino acid sequence at least about 90% identical to the amino acid sequence of SEQ ID NO: 1 or SEQ ID NO:2. The amino acid segment can comprise the amino acid sequence of SEQ ID NO:1 or SEQ ID NO:2. The amino acid sequence of SEQ ID NO:1 or SEQ ID NO:2 can have one or more conservative amino acid substitutions. The amino acid segment can be circular or cyclic. The amino acid segment can be circularized or cyclized via a disulfide bond. The peptide can consist of the amino acid segment. The peptide can selectively home to tumors, sites of injury, and/or sites of blood clots. The peptide can selectively interact with tumors, sites of injury, and/or sites of blood clots.

The amino acid segment can comprise the amino acid sequence of SEQ ID NO:3 or SEQ ID NO: 4, an amino acid sequence at least about 90% identical to the amino acid sequence of SEQ ID NO:3 or SEQ ID NO:4, or the amino acid sequence of SEQ ID NO:3 or SEQ ID NO:4 having one or more conservative amino acid substitutions.

The moiety can be a cancer chemotherapeutic agent, a cytotoxic agent, an anti-angiogenic agent, a polypeptide, a nucleic acid molecule, a small molecule, a fluorophore, fluorescein, rhodamine, a radionuclide, indium-111, technetium-99, carbon-11, carbon-13, or a combination. The moiety can be a therapeutic agent. The moiety can be a detectable agent. The conjugate can comprise a virus. The conjugate can comprise a phage. The conjugate can further comprise a second peptide, wherein the second peptide comprising an amino acid segment comprising the amino acid sequence of SEQ ID NO: 1 or SEQ ID NO: 2, an amino acid sequence at least about 90% identical to the amino acid sequence of SEQ ID NO:1 or SEQ ID NO:2, or the amino acid sequence of SEQ ID NO:1 or SEQ ID NO:2 having one or more conservative amino acid substitutions.

The subject can have cancer, wherein the moiety is directed to tumor stroma in the subject. The conjugate can treat the cancer. The conjugate can have a therapeutic effect on the cancer. The size of a tumor can be reduced. The growth of a tumor can be reduced, stopped or reversed.

The moiety can be used to detect the cancer, visualize one or more tumors, or both. The subject can have one or more sites of injury, wherein the moiety is directed to one or more of the sites of injury. The conjugate can treat at least one of the sites of injury. The conjugate can have a therapeutic effect on at least one of the sites of injury. The moiety can be used to detect, visualize, or image at least one of the sites of injury, or a combination.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION OF THE INVENTION

Figures 1A, 1B, 1C, 1D, 1E, 1F, 1G, 1H, 1I, 1J, 1K, 1L:
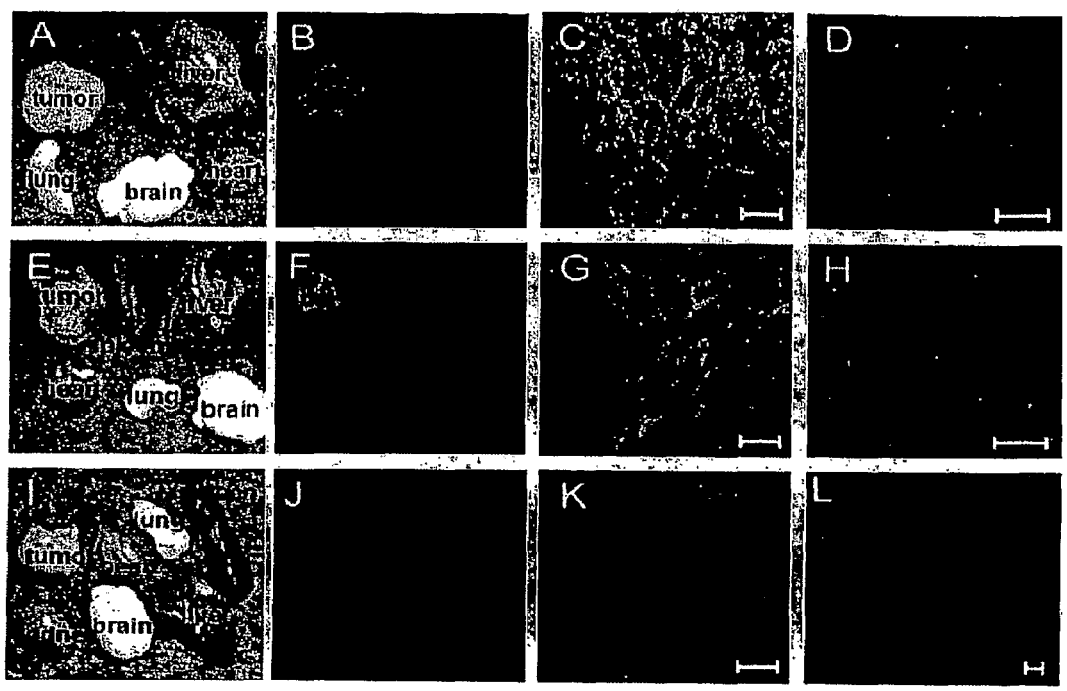
FIGS. 1A to 1M show CLT1 and CLT2 accumulate in tumor interstitial stroma. Mice bearing orthotopic MDA-MB-435 xenograft tumors were intravenously injected with 500 µg of fluorescein-conjugated CLT1, CLT2, or control peptide (KAREC). After 3 h, the mice were perfused with PBS. The tumors and various organs were macroscopically examined for fluorescence under blue light. CLT1 (A, B) and CLT2 (E, F) produced strong fluorescence in excised tumor but not in control organs. Histological analysis (400×) showed that the fluorescein-labeled CLT1 (C) and CLT2 (G) were distributed in a network pattern within the tumor. Fluorescence was strongly reduced when fluorescein-conjugated CLT1 (D) or CLT2 (H) were co-injected with unlabeled CLT2 (5 fold excess). Fluorescein-conjugated control peptide conveyed no fluorescence to the tumors (I-K). Tumor-free tissues of the CLT peptide-injected mice were also negative (L). Representative tissue fluorescence results are shown. Quantification of fluorescence from CLT peptides as fluorescence intensity relative to a control peptide (KAREC) shows that, similar to the MDA-MB-435 tumors (MDA), various other types of tumors specifically bind to intravenously injected CLT peptides (M). Nuclei were stained with DAPI. Error bars show mean±SEM; scale bars 50 µm.

The disclosed method and compositions can be understood more readily by reference to the following detailed description of particular embodiments and the Example included therein and to the Figures and their previous and following description.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. General

The connective tissue (stroma) in and around malignancies is a complex and dynamic structure that integrates the tumor into the host tissue by providing a functional matrix for angiogenesis and lymphangiogenesis, for migrating bystander cells, and for invading tumor cells (Bissell, M. J., Radisky, D. (2001) *Nat. Rev. Cancer* 1, 46-54). Normal connective tissue and its extracellular matrix (ECM) create an anti-proliferative environment, whereas tumor ECM promotes cell migration, survival, and proliferation by providing adhesion proteins, proteases and growth factors critical for these processes (Kalluri, R. (2003) *Nat. Rev. Cancer* 3, 422-33).

The distinctiveness of tumor ECM is reflected in its content of specific markers, such as tenascin (Ventimiglia, J. B., Wikstrand, C. J., Ostrowski, L. E., Bourdon, M. A., Lightner, V. A., & Signer, D. D. (1992) *J. Neuroimmunol.* 36, 41-55) and oncofetal fibronectin (Neri, D., Carnemolla, B., Nissim, A., Leprini, A., Querze, G., Balza, E., Pini, A., Tarli, L., Halin, C., Neri, P., et al. (1997) *Nat. Biotech.* 15, 1271-5). Moreover, high levels of collagen expression (St. Croix, B., Rago, C., Velculescu, V., Traverso, G., Romans, K. E., Montgomery, E., Lal, A., Riggins, G. J., Lengauer, C., Vogelstein, B., et al. (2000) *Science,* 289, 1197-202) and the presence of an alternatively spliced form of fibronectin (Halin, C., Rondini, S., Nilsson, F., Berndt, A., Kosmehl, H., Zardi, L., & Neri, D. (2002) *Nat. Biotechnol.* 20, 264-269) set the ECM of tumor blood vessels apart from that of normal vessels. The interstitial spaces of tumors also contain fibrin, presumably as a result of VEGF-induced leakage of plasma proteins into the tumor tissue (Senger, D. R., Galli, S. J., Dvorak, A. M., Perruzzi, C. A., Harvey, V. S., & H. F. Dvorak. *Science* (1983) 219, 983-985). In a manner similar to wounds, the leaked fibrinogen becomes converted to fibrin by tissue pro-coagulant factors (Dvorak, H. F., Senger, D. R., Dvorak, A. M., Harvey, V. S., & McDonagh, J. (1985) *Science,* 227, 1059-61; Abe, K., Shoji, M., Chen, J., Bierhaus, A., Danave, I., Micko, C., Casper, K., Dillehay, D. L., Nawroth, P. P., & Rickles, F. R. (1999) *Proc. Natl. Acad. Sci. USA* 96, 8663-8).

It has been shown that peptide libraries displayed on phage as a tool to identify peptides that selectively home to tumors in vivo (Ruoslahti, E. (2002) *Nat. Rev. Cancer* 2, 83-90). Homing peptides that are selected by this method can be used as carriers of drugs and imaging agents (Ellerby, H. M., Wadih, A., Ellerby, L. M., Kane R., Andrusiak R., Del Rio, G., Krajewski, S., Lombardo C. R., Rao, R., & Ruoslahti, E. et al. (1999) Nature Medicine 5, 1032-1038; Akerman, M. E., Warren C. W. Chan, W. C. W., Laakkonen, P., Bhatia, S. N., & Ruoslahti E. (2002) Proc. Natl. Acad. Sci. 99, 12617-12621).

The terms "fibrin-binding peptide," "fibronectin-binding peptide," and "clotted plasma protein binding peptide" as used herein refers to any peptide that forms a complex with a clot, soluble or insoluble fibrin or fibronectin, or a soluble or insoluble fragment of fibrin or fibronectin having a structure or characteristic exhibited by fibrin or fibronectin in blood clots. Included among the clot binding peptides are peptides that bind to clot components other than fibrin or fibronectin. The distinguishing characteristic for all these peptides is that they bind to components of blood and plasma clots, but do not substantially bind the corresponding soluble plasma proteins.

A peptide fragment can be prepared by proteolytic digestion of the intact fibrin or fibronectin molecule or a fragment thereof, by chemical peptide synthesis methods well known in the art, by recombinant DNA methods, or by any other method capable of producing a peptide corresponding to a fibrin- or fibronectin-binding peptide.

Specific examples of fibrin and fibronectin-binding peptides are found, for example, in U.S. Pat. Nos. 7,041,790 and 6,984,373, 5,792,742 and PCT application US00/20612, herein incorporated by reference in their entirety for their teachings regarding fibrin and fibronectin-binding peptides.

Phage methodology can also be used to identify peptides that recognize clotted plasma proteins in tumors. A phage library was screened on plasma clots in vitro, and two cyclic decapeptides (CLT1 and CLT2) were derived that specifically home to tumors and wounds in vivo and bind to tumor tissue in overlay of tissue sections. Tissue specificity of the peptides are associated with plasma fibronectin, which becomes bound to fibrin clots. The peptides are useful in targeting of diagnostic and therapeutic agents into tumors and tissue lesions.

Fluorescein conjugates of CLT1 and CLT2 specifically accumulate in tumor tissue after an intravenous injection in multiple cancer models. The peptides also homed to sites of tissue injury. The injected CLT peptides outline a meshwork that co-localizes with fibrin and fibronectin staining, and peptides do not home to tumors grown in mice that lack fibrinogen or plasma fibronectin. The CLT peptides bind to an epitope in a fibrin-fibronectin complex formed as a result of plasma clotting within tumors and at sites of tissue injury.

CLT1 and CLT2 home to tumor stroma, but are not detectable in normal tissues. These peptides also homed to sites of tissue injury, where coagulation typically takes place (Dvorak, H. F., Senger, D. R., Dvorak, A. M., Harvey, V. S., & McDonagh, J. (1985) *Science,* 227, 1059-61; Ten Cate H., Bauer K A., Levi M., Edgington T S., Sublett R D., Barzegar S., Kass B L. & Rosenberg R D. (1993) *J. Clin. Inv.* 92, 1207-12). The meshwork the CLT peptides produced in tumors co-localized with fibrin(ogen) and fibronectin. Finally, the most direct evidence that the CLT peptides detect clotting products in tumors comes from the demonstration that homing of CLT peptides to tumors grown in mice that lack plasma fibronectin, or fibrinogen is greatly reduced. Since the plasma fibronectin-deficient mice do have tissue fibronectin, these results show that the fibronectin required for the CLT binding site is derived from the blood. Therefore, the CLT peptides specifically home to tumors through binding to a binding site that is dependent on the incorporation of fibrin and fibronectin from plasma to tumor interstitium as a result of vascular leakage and tissue clotting activity.

Results indicate that the binding site detected by the CLT peptides in plasma clots is fibronectin. There was no homing of the peptides to tumors grown in mice that lack plasma fibronectin. The CLT peptides homed to some degree to tumors grown in fibrinogen null mice, but the peptide fluorescence was diffuse instead of forming the usual meshwork pattern. Fibronectin contains a number of cryptic binding sites, which become available when the molecule is subjected to tension or interacts with hydrophobic entities (Morla, A., Ruoslahti, E. (1992) *J. Cell. Biol.* 118, 421-9; Baneyx, G., Baugh, L., & Vogel, V. (2001) *Proc. Natl. Acad. Sci. USA* 98, 14464-8). Nonetheless, these results are compatible with the CLT binding site being on fibronectin, and that the organization of plasma-derived fibronectin, and perhaps also its retention, in tumor stroma, requires simultaneous fibrin deposition of a fibrin meshwork.

The CLT peptides recognized every tumor tested, including five tumor types in mouse and some human tumors. Thus, the CLT peptides are useful as imaging or drug delivery agent for tumors, as well as for tissue injuries.

Based on these findings, disclosed are homing molecules and conjugates useful, for example, for directing a moiety to tumors, including tumor stroma, to wound sites and sites of injury, and to blood clots, for reducing the size and/or number of tumors in a subject, for reducing the number of tumor vessels in a subject, for reducing infection and delivering therapeutics to a wound site, for imaging and/or delivering therapeutics to blood clots, and for treating cancer. The disclosed conjugates also can be useful, for example, for imaging tumors, including tumor stroma, as well as sites of tissue injury and blood clots. In particular, blood clots such as ones found in heart infarct, stroke and venous thrombosis can be targeted with the disclosed homing molecules and conjugates. The disclosed methods can be used to detect, visualize, image such blood clots and/or deliver therapeutics, such as thrombolytic agents, to such blood clots. Any fibrin-binding peptide, or any peptide that binds to fibronectin in the context of a blood or plasma clot, or any peptide capable of binding to another clotted plasma protein is useful with the methods disclosed herein.

B. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Materials

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular peptide is disclosed and discussed and a number of modifications that can be made to a number of molecules including the peptide are discussed, specifically contemplated is each and every combination and permutation of the peptides and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Disclosed are methods and compositions related to an isolated peptide comprising an amino acid segment comprising the amino acid sequence of SEQ ID NO: 1 or SEQ ID NO: 2 or related amino acid sequences.

Also disclosed are isolated peptides comprising an amino acid segment comprising; for example, the amino acid sequence of SEQ ID NO: 1 or SEQ ID NO: 2, an amino acid sequence at least about 90% identical to the amino acid sequence of SEQ ID NO:1 or SEQ ID NO:2, or the amino acid sequence of SEQ ID NO:1 or SEQ ID NO:2 having one or more conservative amino acid substitutions.

Also disclosed are conjugates, wherein the conjugate comprises a moiety linked to a peptide comprising an amino acid segment comprising, for example, the amino acid sequence of SEQ ID NO: 1 or SEQ ID NO: 2, an amino acid sequence at least about 90% identical to the amino acid sequence of SEQ ID NO:1 or SEQ ID NO:2, or the amino acid sequence of SEQ ID NO:1 or SEQ ID NO:2 having one or more conservative amino acid substitutions.

The peptide can have a length of less than 100 residues. The peptide can have a length of less than 50 residues. The peptide can have a length of less than 20 residues. The amino acid segment can comprise an amino acid sequence at least about 90% identical to the amino acid sequence of SEQ ID NO: 1 or SEQ ID NO:2. The amino acid segment can comprise the amino acid sequence of SEQ ID NO:1 or SEQ ID NO:2. The amino acid sequence of SEQ ID NO:1 or SEQ ID NO:2 can have one or more conservative amino acid substitutions. The amino acid segment can be circular or cyclic. The amino acid segment can be circularized or cyclized via a disulfide bond. The peptide can consist of the amino acid segment. The peptide can selectively home to tumors, sites of injury, and/or sites of blood clots. The peptide can selectively interact with tumors, sites of injury, and/or sites of blood clots.

The amino acid segment can comprise, for example, the amino acid sequence of SEQ ID NO:3 or SEQ ID NO: 4, an amino acid sequence at least about 90% identical to the amino acid sequence of SEQ ID NO:3 or SEQ ID NO:4, or the amino acid sequence of SEQ ID NO:3 or SEQ ID NO:4 having one or more conservative amino acid substitutions.

The moiety can be a cancer chemotherapeutic agent, a cytotoxic agent, an anti-angiogenic agent, a polypeptide, a nucleic acid molecule, a small molecule, a fluorophore, fluorescein, rhodamine, a radionuclide, indium-111, technetium-99, carbon-11, carbon-13, or a combination. The moiety can be a therapeutic agent. The moiety can be a detectable agent. The conjugate can comprises a virus. The conjugate can comprise a phage. The conjugate can further comprise a second peptide, wherein the second peptide comprising an amino acid segment comprising the amino acid sequence of SEQ ID NO: 1 or SEQ ID NO: 2, an amino acid sequence at least about 90% identical to the amino acid sequence of SEQ ID NO:1 or SEQ ID NO:2, or the amino acid sequence of SEQ ID NO:1 or SEQ ID NO:2 having one or more conservative amino acid substitutions.

The subject can have cancer, wherein the moiety is directed to tumor stroma in the subject. The conjugate can treat the cancer. The conjugate can have a therapeutic effect on the cancer. The size of a tumor can be reduced. The growth of a tumor can be reduced, stopped or reversed.

The moiety can be used to detect the cancer, visualize one or more tumors, or both. The subject can have one or more sites of injury, wherein the moiety is directed to one or more of the sites of injury. The conjugate can treat at least one of the sites of injury. The conjugate can have a therapeutic effect on at least one of the sites of injury. The moiety can be used to detect, visualize, or image at least one of the sites of injury, or a combination. The subject can have one or more blood clots, wherein the moiety is directed to one or more of the blood clots. The conjugate can treat at least one of the blood clots. The conjugate can have a therapeutic effect on at least one of the blood clots. The moiety can be used to detect, visualize, or image at least one blood clot.

A. Homing Molecules

Disclosed are homing molecules that selectively home to tumors, including tumor stroma, sites of injuries and wounds, and blood clots. A variety of homing molecules can be used in the disclosed compositions, conjugates and methods. Such homing molecules include, without limitation, peptides as disclosed herein. Any fibrin-binding peptide, or any peptide that binds to fibronectin in the context of a blood or plasma clot, or any peptide capable of binding to another clotted plasma protein and capable of homing is useful with the methods disclosed herein.

The disclosed compounds, compositions, conjugates and methods can include or use the disclosed homing molecules in various forms, including peptides and peptidomimetics as disclosed. For convenience of expression, in many places herein the use or inclusion of peptides will be recited. It is understood that, in such cases, it is considered that homing molecules in various forms can also be used or included in the same or similar ways as is described in terms of peptides, and such use and inclusion is specifically contemplated and disclosed thereby.

As used herein, the term "molecule" is used broadly to mean a polymeric or non-polymeric organic chemical such as a small molecule drug; a nucleic acid molecule such as an RNA, a DNA such as a cDNA or oligonucleotide; a peptide; or a protein such as a growth factor receptor or an antibody or fragment thereof such as an Fv, Fd, or Fab fragment or another antibody fragment containing the antigen-binding domain.

The term "homing molecule" as used herein, means any molecule that selectively homes in vivo to the clotted plasma of one or more tumors, wound tissue, or blood clots in preference to normal tissue. Similarly, the term "homing peptide" or "homing peptidomimetic" means a peptide that selectively homes in vivo to the stroma of one or more tumors in preference to normal tissue. Any fibrin-binding peptide, or any peptide that binds to fibronectin in the context of a blood or plasma clot, or any peptide capable of binding to another clotted plasma protein is useful with the methods disclosed herein. It is understood that a homing molecule that selectively homes in vivo to tumor stroma can home to the stroma of all tumors or can exhibit preferential homing to the stroma of one or a subset of tumor types.

By "selectively homes" is meant that, in vivo, the homing molecule binds preferentially to the target as compared to non-target. For example, the homing molecule can bind preferentially to clotted plasma of one or more tumors, wound tissue, or blood clots, including tumor stroma, such as breast tumor stroma, as compared to non-tumoral tissue or non-wound tissue. Such a homing molecule can selectively home, for example, to tumor stroma. Selective homing to, for example, tumor stroma generally is characterized by at least a two-fold greater localization within tumor stroma, such as breast tumor stroma, as compared to several tissue types of non-tumor tissue. A homing molecule can be characterized by 5-fold, 10-fold, 20-fold or more preferential localization to tumor stroma as compared to several or many tissue types of non-tumoral tissue, or as compared to-most or all non-tumoral tissue. Thus, it is understood that, in some cases, a homing molecule homes, in part, to the stroma of one or more normal organs in addition to homing to breast and other tumor stroma. Selective homing can also be referred to as targeting.

In some embodiments, a homing molecule can be a molecule that selectively homes to tumor stroma, wounds, or plasma clots and which is not an antibody or antigen-binding fragment thereof. The term "antibody" is an art-recognized term that refers to a peptide or polypeptide containing one or more complementarity determining regions (CDRs). See, for example, Borrabaeck, Antibody Engineering 2nd Edition, Oxford University Press, New York (1995).

Homing, including preferential and/or selective homing, does not mean that the homing molecule does not bind to any normal and/or non-targeted areas (for example, non-tumor, non-clot, and/or non-wound). In some embodiments, homing selectivity can be, for example, at least about 20-fold, at least about 30-fold, at least about 50-fold, at least about 75-fold, at least about 100-fold, at least about 150-fold, or at least about 200-fold selective for a corresponding target in terms of relative $K_i$ over other non-target components. In some embodiments, the homing molecule can have at least about a 50-fold selectivity, at least about a 100-fold selectivity, at least about a 200-fold selectivity, at least about a 300-fold selectivity, at least about a 400-fold selectivity, at least about a 500-fold selectivity, at least about a 600-fold selectivity, at least about a 700-fold selectivity, at least about an 800-fold selectivity, at least about a 1000-fold selectivity, or at least about a 1500-fold selectivity to a corresponding target. For example, in some preferred embodiments, the homing molecule can have a $K_i$ value against a target of less than about 200 nM, less than about 150 nM, less than about 100 nM, or less than about 75 nM. In some preferred embodiments, the homing molecule can have a $K_i$ value against a target of more than about 50 nM, more than about 25 nM, more than about 20 nM, more than about 15 nM, more than about 10 nM, more than about 5 nM, more than about 3 nM, or more than about 1 nM. In some preferred embodiments, the targeting moiety binds its target with a $K_D$ less than about $10^{-8}$ M, less than about $10^{-9}$ M, less than about $10^{-10}$ M, less than about $10^{-11}$ M, less than about $10^{-12}$ M, less than about $10^{-13}$ M, or less than about $10^{-14}$ M.

Binding in the context of a homing molecule recognizing and/or binding to its target can refer to both covalent and non-covalent binding, for example where a homing molecule can bind, attach or otherwise couple to its target by covalent and/or non-covalent binding. Binding can be either high affinity or low affinity, preferably high affinity. Examples of binding forces that can be useful include, but are not limited to, covalent bonds, dipole interactions, electrostatic forces, hydrogen bonds, hydrophobic interactions, ionic bonds, and/or van der Waals forces.

1. Peptides and Peptidomimetics

Disclosed are methods and compositions related to an isolated peptide comprising an amino acid segment comprising the amino acid sequence of SEQ ID NO: 1 or SEQ ID NO: 2 or related amino acid sequences. The isolated peptides can comprise, for example, an amino acid segment comprising, for example, the amino acid sequence of SEQ ID NO: 1 or SEQ ID NO: 2, an amino acid sequence at least about 90% identical to the amino acid sequence of SEQ ID NO:1 or SEQ ID NO:2, or the amino acid sequence of SEQ ID NO:1 or SEQ ID NO:2 having one or more conservative amino acid substitutions. The amino acid segment can comprise, for example, the amino acid sequence of SEQ ID NO:3 or SEQ ID NO: 4, an amino acid sequence at least about 90% identical to the amino acid sequence of SEQ ID NO:3 or SEQ ID NO:4, or the amino acid sequence of SEQ ID NO:3 or SEQ ID NO:4 having one or more conservative amino acid substitutions.

The amino acid segment can comprise an amino acid sequence at least about 90%, 80%, 70%, or 60% identical to the amino acid sequence of SEQ ID NO: 1, SEQ ID NO:2, SEQ ID NO:3, or SEQ ID NO:4. The amino acid segment can comprise the amino acid sequence of SEQ ID NO:1, SEQ ID NO:2, SEQ ID NO:3, or SEQ ID NO:4. The amino acid segment can comprise the amino acid sequence of SEQ ID NO:1, SEQ ID NO:2, SEQ ID NO:3, or SEQ ID NO:4 having one, two, three, four, five, six, seven, eight, or nine conservative amino acid substitutions. The amino acid segment can comprise a chimera of the amino acid sequence SEQ ID NO:1 or SEQ ID NO:2. Such a chimera can be additive, where sequence of one sequence is added to another sequence, substitutional, where sequence of one sequence is substituted for sequence of another sequence, or a combination. The disclosed peptides can consist of the amino acid segment.

The amino acid segment can be linear, circular or cyclic. The amino acid segment can be circularized or cyclized via any suitable linkage, for example, a disulfide bond.

The peptide can have any suitable length, such as a length of less than 100 residues. The peptide can have a length of less than 50 residues. The peptide can have a length of less than 20 residues.

The disclosed peptides can selectively home to tumors, sites of injury, and/or sites of blood clots. The disclosed peptides can selectively interact with tumors, sites of injury, and/or sites of blood clots.

Also disclosed are isolated peptides which has a length of less than 100 residues and which includes the amino acid sequence CLT1 (SEQ ID NO: 1) or a peptidomimetic thereof, or CLT2 (SEQ ID NO: 2) or a peptidomimetic thereof. Such an isolated peptide can have, for example, a length of less than 50 residues or a length of less than 20 residues. In particular embodiments, disclosed can be a peptide that includes the amino acid sequence SEQ ID NO: 1 or SEQ ID NO: 2, and has a length of less than 20, 50 or 100 residues.

The disclosed peptides can be in isolated form. As used herein in reference to the disclosed peptides, the term "isolated" means a peptide that is in a form that is relatively free from material such as contaminating polypeptides, lipids, nucleic acids and other cellular material that normally is associated with the peptide in a cell or that is associated with the peptide in a library or in a crude preparation.

The disclosed peptides can have any suitable length. The disclosed peptides can have, for example, a relatively short length of less than six, seven, eight, nine, ten, 12, 15, 20, 25, 30, 35 or 40 residues. The disclosed peptides also can be useful in the context of a significantly longer sequence. For example, as disclosed herein, the CLT1 and CLT2 peptides (SEQ ID NO: 1 and SEQ ID NO: 2, respectively) maintained the ability to home when fused to a phage coat protein, confirming that the disclosed peptides can have selective horning activity when embedded in a larger protein sequence. Thus, the peptides can have, for example, a length of up to 50, 100, 150, 200, 250, 300, 400, 500, 1000 or 2000 residues. In particular embodiments, a peptide can have a length of at least 10, 20, 30, 40, 50, 60, 70, 80, 90, 100 or 200 residues. In further embodiments, a peptide can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

i. Peptide Variants

As discussed herein there are numerous variants of the CLT1 and CLT2 peptides that are herein contemplated, as well as other fibrin, clotted fibronectin, or clotted plasma protein binding peptides. In addition to the known functional variants there are derivatives of the peptides which can also function in the disclosed methods and compositions. Protein and peptide variants and derivatives are well understood by those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues.

Deletions are characterized by the removal of one or more amino acid residues from the protein or peptide sequence. Typically, no more than about from 2 to 6 residues are deleted at any one site within the protein or peptide molecule. These variants can be prepared by site specific mutagenesis of nucleotides in the DNA encoding the protein or peptide, thereby producing DNA encoding the variant, and thereafter expressing the DNA in recombinant cell culture. Techniques for making substitution mutations at predetermined sites in DNA having a known sequence are well known. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure. Substitutional variants are those in which at least one residue has been removed and a different residue inserted in its place.

As used herein in reference to a specified amino acid sequence, a "conservative variant" is a sequence in which a first amino acid is replaced by another amino acid or amino acid analog having at least one biochemical property similar to that of the first amino acid; similar properties include, for example, similar size, charge, hydrophobicity or hydrogen-bonding capacity.

As an example, a conservative variant can be a sequence in which a first uncharged polar amino acid is conservatively substituted with a second (non-identical) uncharged polar amino acid such as cysteine, serine, threonine, tyrosine, glycine, glutamine or asparagine or an analog thereof. A conservative variant also can be a sequence in which a first basic amino acid is conservatively substituted with a second basic amino acid such as arginine, lysine, histidine, 5-hydroxylysine, N-methyllysine or an analog thereof. Similarly, a conservative variant can be a sequence in which a first hydrophobic amino acid is conservatively substituted with a second hydrophobic amino acid such as alanine, valine, leucine, isoleucine, proline, methionine, phenylalanine or tryptophan or an analog thereof. In the same way, a conservative variant can be a sequence in which a first acidic amino acid is conservatively substituted with a second acidic amino acid such as aspartic acid or glutamic acid or an analog thereof; a sequence in which an aromatic amino acid such as phenylalanine is conservatively substituted with a second aromatic amino acid or amino acid analog, for example, tyrosine; or a sequence in which a first relatively small amino acid such as alanine is substituted with a second relatively small amino acid or amino acid analog such as glycine or valine or an analog thereof. For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein. As non-limiting examples, conservative variants of CLT1 (CGLIIQKNEC, SEQ ID NO:1) and CLT2 (CNAGESSKNC, SEQ ID NO:2) include CALIIQKNEC (SEQ ID NO:13), CGLILQKNEC (SEQ ID NO:14), CGLIIQRNEC (SEQ ID NO:15), CGLIINKNEC (SEQ ID NO:16), CNAAESSKNC (SEQ ID NO:17), CNAGESSRNC (SEQ ID NO:18), CNAGESTKNC (SEQ ID NO:19), and CNAGDSSKNC (SEQ ID NO:20). It is understood that conservative variants of both CLT1 and CLT2 (SEQ ID NOs: 1 and 2) encompass sequences containing one, two, three, four or more amino acid substitutions relative to SEQ ID NO: 1 and 2, and that such variants can include naturally and non-naturally occurring amino acid analogs.

Substantial changes in function or immunological identity are made by selecting substitutions that are less conservative, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

Substitutional or deletional mutagenesis can be employed to insert sites for N-glycosylation (Asn-X-Thr/Ser) or O-glycosylation (Ser or Thr). Deletions of cysteine or other labile residues also can be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO: 1 sets forth a particular sequence of CLT1 and SEQ ID NO: 2 sets forth a particular sequence of CLT2. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Also disclosed is a peptide wherein the amino acid segment comprises the amino acid sequence of SEQ ID NO:3 or SEQ ID NO: 4, an amino acid sequence at least about 90% identical to the amino acid sequence of SEQ ID NO:3 or SEQ ID NO:4, or the amino acid sequence of SEQ ID NO:3 or SEQ ID NO:4 having one or more conservative amino acid substitutions.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent than those discussed above. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $—CH_2NH—$, $—CH_2S—$, $—CH_2—CH_2—$, $—CH=CH—$ (cis and trans), $—COCH_2—$, $—CH(OH)CH_2—$, and $—CHH_2SO—$ (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) ($—CH_2NH—$, $CH_2CH_2—$); Spatola et al. Life Sci 38:1243-1249 (1986) ($—CH\ H_2—S$); Hann J. Chem. Soc Perkin Trans. I 307-314 (1982) (CH—CH—, cis and trans); Almquist et al. J. Med. Chem. 23:1392-1398 (1980) ($—COCH_2$); Jennings-White et al. Tetrahedron Lett 23:2533 (1982) ($—COCH_2—$); Szelke et al. European Appln, EP 45665 CA (1982): 97:39405 (1982) ($—CH(OH)CH_2—$); Holladay et al. Tetrahedron. Lett 24:4401-4404 (1983) ($—C(OH)CH_2—$); and Hruby Life Sci 31:189-199 (1982) ($—CH_2—S—$); each of which is incorporated herein by reference. A particularly preferred non-peptide linkage is $—CH_2NH—$. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Also disclosed are chimeric proteins containing a disclosed peptide fused to a heterologous protein. In one embodiment, the heterologous protein can have a therapeutic activity such as cytokine activity, cytotoxic activity or pro-apoptotic activity. In a further embodiment, the heterologous protein can be an antibody or antigen-binding fragment thereof. In other embodiments, the chimeric protein includes a peptide containing the amino acid sequence SEQ ID NO: 1 or SEQ ID NO: 2, or a conservative variant or peptidomimetic thereof, fused to a heterologous protein. The term "heterologous," as used herein in reference to a protein fused to the disclosed peptides, means a protein derived from a source other than the gene encoding the peptide or from which the peptidomimetic is derived. The disclosed chimeric proteins can have a variety of lengths including, but not limited to, a length of less than 100 residues, less than 200 residues, less than 300 residues, less than 400 residues, less than 500 residues, less than 800 residues or less than 1000 residues.

As used herein, "chimera" and "chimeric" refer to any combination of sequences derived from two or more sources. This includes, for example, from single moiety of subunit (e.g., nucleotide, amino acid) up to entire source sequences added, inserted and/or substituted into other sequences. Chimeras can be, for example, additive, where one or more portions of one sequence are added to one or more portions of one or more other sequences; substitutional, where one or more portions of one sequence are substituted for one or more portions of one or more other sequences; or a combination. "Conservative substitutional chimeras" can be used to refer to substitutional chimeras where the source sequences for the chimera have some structural and/or functional relationship and where portions of sequences having similar or analogous structure and/or function are substituted for each other. Typical chimeric and humanized antibodies are examples of conservative substitutional chimeras.

Also disclosed are bifunctional peptides which contains a homing peptide fused to a second peptide having a separate function. Such bifunctional peptides have at least two functions conferred by different portions of the full-length molecule and can, for example, display anti-angiogenic activity or pro-apoptotic activity in addition to selective homing activity.

Also disclosed are isolated multivalent peptides that includes at least two subsequences each independently containing a homing molecule (for example, the amino acid sequence SEQ ID NO: 1 or 2, or a conservative variant or peptidomimetic thereof). The multivalent peptide can have, for example, at least three, at least five or at least ten of such subsequences each independently containing a homing molecule (for example, the amino acid sequence of SEQ ID NO: 1 or 2, or a conservative variant or peptidomimetic thereof). In particular embodiments, the multivalent peptide can have two, three, four, five, six, seven, eight, nine, ten, fifteen or twenty identical or non-identical subsequences. In a further embodiment, the multivalent peptide can contain identical subsequences, which consist of a homing molecule (for example, the amino acid sequence SEQ ID NO: 1 or 2, or a conservative variant or peptidomimetic thereof). In a further embodiment, the multivalent peptide contains contiguous identical or non-identical subsequences, which are not separated by any intervening amino acids. In yet further embodiments, the multivalent peptide can be cyclic or otherwise conformationally constrained. In one example, the peptide can be circularized or cyclized via a disulfide bond.

As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as selective homing activity of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α-dialkylglycine or α-aminocycloalkane carboxylic acid; an $N^\alpha$—$C^\alpha$cyclized amino acid; an $N^\alpha$-methylated amino acid; a β- or γ-amino cycloalkane carboxylic acid; an α,β-unsaturated amino acid; a β,β-dimethyl or β-methyl amino acid; a β-substituted-2,3-methano amino acid; an N—$C^\epsilon$ or $C^\alpha$—$C^\Delta$ cyclized amino acid; a substituted proline or another amino acid mimetic. A peptidomimetic which mimics peptide secondary structure can contain, for example, a non-peptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. As an example, the Cambridge Structural Database contains a collection of greater than 300,000 compounds that have known crystal structures (Allen et al., Acta Crystalloqr. Section B, 35:2331 (1979)). This structural depository is continually updated as new crystal structures are determined and can be screened for compounds having suitable shapes, for example, the same shape as a disclosed peptide, as well as potential geometrical and chemical complementarity to a target molecule. Where no crystal structure of a peptide or a target molecule that binds the peptide is available, a structure can be generated using, for example, the program CONCORD (Rusinko et al., J. Chem. Inf. Comput. Sci. 29:251 (1989)). Another database, the Available Chemicals Directory (Molecular Design Limited, Information Systems; San Leandro Calif.), contains about 100,000 compounds that are commercially available and also can be searched to identify potential peptidomimetics of a peptide, for example, with activity in selectively homing to tumor stroma, wounds, and plasma clots.

If desired, an isolated peptide, or a homing molecule as discussed further elsewhere herein, can be cyclic or otherwise conformationally constrained. As used herein, a "conformationally constrained" molecule, such as a peptide, is one in which the three-dimensional structure is maintained substantially in one spatial arrangement over time. Conformationally constrained molecules can have improved properties such as increased affinity, metabolic stability, membrane permeability or solubility. Methods of conformational constraint are well known in the art and include cyclization as discussed further elsewhere herein.

As used herein in reference to a peptide, the term "cyclic" means a structure including an intramolecular bond between two non-adjacent amino acids or amino acid analogues. The cyclization can be effected through a covalent or non-covalent bond. Intramolecular bonds include, but are not limited to, backbone to backbone, side-chain to backbone and side-chain to side-chain bonds. A preferred method of cyclization is through formation of a disulfide bond between the side-chains of non-adjacent amino acids or amino acid analogs. Residues capable of forming a disulfide bond include, for example, cysteine (Cys), penicillamine (Pen), β,β-pentamethylene cysteine (Pmc), β,β-pentamethylene-β-mercaptopropionic acid (Pmp) and functional equivalents thereof.

A peptide also can cyclize, for example, via a lactam bond, which can utilize a side-chain group of one amino acid or analog thereof to form a covalent attachment to the N-terminal amine of the amino-terminal residue. Residues capable of forming a lactam bond include aspartic acid (Asp), glutamic acid (Glu), lysine (Lys), ornithine (orn), α,β-diamino-propionic acid, γ-amino-adipic acid (Adp) and M-(aminomethyl)benzoic acid (Mamb). Cyclization additionally can be effected, for example, through the formation of a lysinonorleucine bond between lysine (Lys) and leucine (Leu) residues or a dityrosine bond between two tyrosine (Tyr) residues. The skilled person understands that these and other bonds can be included in a cyclic peptide.

B. Conjugates

Disclosed are conjugates comprising a moiety and a homing molecule, such as a peptide as disclosed herein. For example, disclosed are conjugates containing a therapeutic agent linked to a homing molecule that selectively homes to tumor stroma, wounds, and plasma clots. Disclosed conjugates can comprise, for example, a moiety linked to a peptide. The peptide can be any of those discussed herein, such as fibrin-binding peptides, clotted fibronectin-binding peptides, or clotted plasma protein binding peptides. In some forms, the peptide can comprise an amino acid segment comprising, for example, the amino acid sequence of SEQ ID NO: 1 or SEQ ID NO: 2, an amino acid sequence at least about 90% identical to the amino acid sequence of SEQ ID NO:1 or SEQ ID NO:2, or the amino acid sequence of SEQ ID NO:1 or SEQ ID NO:2 having one or more conservative amino acid substitutions.

Any form or type of homing molecule as disclosed herein can be used in the disclosed conjugates. The moiety can be any molecule. Preferably the moiety is a molecule that is usefully targeted to the target of the homing molecule. For example, moieties that affect the target, such as moieties with therapeutic effect, or that facilitate detection, visualization or imaging of the target, such as fluorescent molecule or radionuclides. Disclosed peptides that home to tumors, wound sites, and blood clots can be usefully combined with, for example, moieties that can, for example, affect tumors and cancer, reduce or eliminate blood clots, and/or promote wound healing. A variety of therapeutic agents are useful in the conjugates including, without limitation, cancer chemotherapeutic agents, cytotoxic agents, anti-angiogenic agents, polypeptides, nucleic acid molecules and small molecules.

A conjugate containing multiple homing molecules can include, for example, two or more, three or more, five or more, ten or more, twenty or more, thirty or more, forty or more, fifty or more, 100 or more, 200 or more, 300 or more, 400 or more, 500 or more, or 1000 or more homing molecules. In one embodiment, the conjugate includes homing molecules that all have an identical amino acid sequence. In another embodiment, the conjugate includes homing molecules having two or more non-identical amino acid sequences. For example, SEQ ID NO: 1 and SEQ ID NO: 2 can be used separately or together. Moieties useful in a conjugate incorporating multiple homing molecules include, without limitation, phage, retroviruses, adenoviruses, adeno-associated viruses and other viruses, cells, liposomes, polymeric matrices, non-polymeric matrices, particles such as gold particles, microdevices, nanodevices, and nano-scale semiconductor materials.

A conjugate can contain, for example, a liposome or other polymeric matrix linked to at least two homing molecules. If desired, the liposome or other polymeric matrix can be linked to at least ten, at least 100 or at least 1000 homing molecules. Liposomes can be useful in such conjugates; liposomes consist of phospholipids or other lipids, are nontoxic, physiologically acceptable and metabolizable carriers that are relatively simple to make and administer (Gregoriadis, Liposome Technology, Vol. 1 (CRC Press, Boca Raton, Fla. (1984)). The liposome or other polymeric matrix can optionally include another component such as, without limitation, a therapeutic agent, cancer chemotherapeutic agent, cytotoxic agent, anti-angiogenic agent, polypeptide or nucleic acid molecule.

Components of the disclosed conjugates can be combined, linked and/or coupled in any suitable manner. For example, moieties and homing molecules can be associated covalently or non-covalently, directly or indirectly, with or without a linker moiety.

C. Moieties

Disclosed are compositions and methods of directing a moiety to a target. As used herein, the term "moiety" is used broadly to mean a physical, chemical, or biological material that generally imparts a biologically useful function to a linked molecule. A moiety can be any natural or nonnatural material including, without limitation, a biological material, such as a cell, phage or other virus; an organic chemical such as a small molecule; a radionuclide; a nucleic acid molecule or oligonucleotide; a polypeptide; or a peptide. Useful moieties include, yet are not limited to, therapeutic agents such as cancer chemotherapeutic agents, cytotoxic agents, pro-apoptotic agents, and anti-angiogenic agents; detectable labels and imaging agents; and tags or other insoluble supports. Useful moieties further include, without limitation, phage and other viruses, cells, liposomes, polymeric matrices, non-polymeric matrices or particles such as gold particles, microdevices and nanodevices, and nano-scale semiconductor materials. These and other moieties known in the art can be components of a conjugate.

1. Therapeutic Agents

The moiety incorporated into a conjugate can be a therapeutic agent. As used herein, the term "therapeutic agent" means a molecule which has one or more biological activities in a normal or pathologic tissue. A variety of therapeutic agents can be included in a conjugate.

In some embodiments, a conjugate can contains a cancer chemotherapeutic agent. As used herein, a "cancer chemotherapeutic agent" is a chemical agent that inhibits the proliferation, growth, life-span or metastatic activity of cancer cells. Such a cancer chemotherapeutic agent can be, without limitation, a taxane such as docetaxel; an anthracyclin such as doxorubicin; an alkylating agent; a vinca alkaloid; an anti-metabolite; a platinum agent such as cisplatin or carboplatin; a steroid such as methotrexate; an antibiotic such as adriamycin; a isofamide; or a selective estrogen receptor modulator; an antibody such as trastuzumab.

Taxanes are chemotherapeutic agents useful in the conjugates. Useful taxanes include, without limitation, docetaxel (Taxotere; Aventis Pharmaceuticals, Inc.; Parsippany, N.J.) and paclitaxel (Taxol; Bristol-Myers Squibb; Princeton, N.J.). See, for example, Chan et al., J. Clin. Oncol. 17:2341-2354 (1999), and Paridaens et al., J. Clin. Oncol. 18:724 (2000).

A cancer chemotherapeutic agent useful in a conjugate also can be an anthracyclin such as doxorubicin, idarubicin or daunorubicin. Doxorubicin is a commonly used cancer chemotherapeutic agent and can be useful, for example, for treating breast cancer (Stewart and Ratain, In: "Cancer: Principles and practice of oncology" 5th ed., chap. 19 (eds. DeVita, Jr., et al.; J. P. Lippincott 1997); Harris et al., In "Cancer: Principles and practice of oncology," supra, 1997). In addition, doxorubicin has anti-angiogenic activity (Folkman, Nature Biotechnology 15:510 (1997); Steiner, In "Angiogenesis: Key principles—Science, technology and medicine," pp. 449-454 (eds. Steiner et al.; Birkhauser Verlag, 1992)), which can contribute to its effectiveness in treating cancer.

An alkylating agent such as melphalan or chlorambucil also can be a cancer chemotherapeutic agent useful in a conjugate. Similarly, a vinca alkaloid such as vindesine, vinblastine or vinorelbine; or an antimetabolite such as 5-fluorouracil, 5-fluorouridine or a derivative thereof can be a cancer chemotherapeutic agent useful in a conjugate.

A platinum agent also can be a cancer chemotherapeutic agent useful in the conjugates. Such a platinum agent can be, for example, cisplatin or carboplatin as described, for example, in Crown, Seminars in Oncol. 28:28-37 (2001). Other cancer chemotherapeutic agents useful in a conjugate include, without limitation, methotrexate, mitomycin-C, adriamycin, ifosfamide and ansamycins.

A cancer chemotherapeutic agent for treatment of breast cancer and other hormonally-dependent cancers also can be an agent that antagonizes the effect of estrogen, such as a selective estrogen receptor modulator or an anti-estrogen. The selective estrogen receptor modulator, tamoxifen, is a cancer chemotherapeutic agent that can be used in a conjugate for treatment of breast cancer (Fisher et al., J. Natl. Cancer Instit. 90:1371-1388 (1998)).

A therapeutic agent useful in a conjugate can be an antibody such as a humanized monoclonal antibody. As an example, the anti-epidermal growth factor receptor 2 (HER2) antibody, trastuzumab (Herceptin; Genentech, South San Francisco, Calif.) is a therapeutic agent useful in a conjugate for treating HER2/neu overexpressing breast cancers (White et al., Annu. Rev. Med. 52:125-141 (2001)).

Useful therapeutic agents also can be a cytotoxic agent, which, as used herein, can be any molecule that directly or indirectly promotes cell death. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab; antimicrobial peptides such as those described further below; pro-apoptotic polypeptides such as caspases and toxins, for example, caspase-8; diphtheria toxin A chain, *Pseudomonas* exotoxin A, cholera toxin, ligand fusion toxins such as DAB389EGF, *ricinus communis* toxin (ricin); and cytotoxic cells such as cytotoxic T cells. See, for example, Martin et al., Cancer Res. 60:3218-3224 (2000); Kreitman and Pastan, Blood 90:252-259 (1997); Allam et al., Cancer Res. 57:2615-2618 (1997); and Osborne and Coronado-Heinsohn, Cancer J. Sci. Am. 2:1.75 (1996). One skilled in the art understands that these and additional cytotoxic agents described herein or known in the art can be useful in the disclosed conjugates and methods.

In one embodiment, a therapeutic agent can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic polypeptides; and anti-angiogenic polypeptides. As non-limiting examples, useful therapeutic polypeptides can be a cytokine such as tumor necrosis factor-α (TNF-α), tumor necrosis factor-β (TNF-β), granulocyte macrophage colony stimulating factor (GM-CSF), granulocyte colony stimulating factor (G-CSF), interferon .alpha. (IFN-α); interferon .gamma. (IFN-γ), interleukin-1 (IL-1), interleukin-2 (IL-2), interleukin-3 (IL-3), interleukin-4 (IL-4), interleukin-6 (IL-6), interleukin-7 (IL-7), interleukin-10 (IL-10), interleukin-12 (IL-12), lymphotactin (LTN) or dendritic cell chemokine 1 (DC-CK1); an anti-HER2 antibody or fragment thereof; a cytotoxic polypeptide including a toxin or caspase, for example, diphtheria toxin A chain, *Pseudomonas* exotoxin A, cholera toxin, a ligand fusion toxin such as DAB389EGF or ricin; or an anti-angiogenic polypeptide such as angiostatin, endostatin, thrombospondin, platelet factor 4; anastellin; or one of those described further herein or known in the art (see below). It is understood that these and other polypeptides with biological activity can be a "therapeutic polypeptide."

A therapeutic agent useful in a conjugate also can be an anti-angiogenic agent. As used herein, the term "anti-angiogenic agent" means a molecule that reduces or prevents angiogenesis, which is the growth and development of blood vessels. A variety of anti-angiogenic agents can be prepared by routine methods. Such anti-angiogenic agents include, without limitation, small molecules; proteins such as dominant negative forms of angiogenic factors, transcription factors and antibodies; peptides; and nucleic acid molecules including ribozymes, antisense oligonucleotides, and nucleic acid molecules encoding, for example, dominant negative forms of angiogenic factors and receptors, transcription factors, and antibodies and antigen-binding fragments thereof. See, for example, Hagedorn and Bikfalvi, Crit. Rev. Oncol. Hematol. 34:89-110 (2000), and Kirsch et al., J. Neurooncol. 50:149-163 (2000).

Vascular endothelial growth factor (VEGF) has been shown to be important for angiogenesis in many types of cancer, including breast cancer angiogenesis in vivo (Borgstrom et al., Anticancer Res. 19:4213-4214 (1999)). The biological effects of VEGF include stimulation of endothelial cell proliferation, survival, migration and tube formation, and regulation of vascular permeability. An anti-angiogenic agent can be, for example, an inhibitor or neutralizing antibody that reduces the expression or signaling of VEGF or another angiogenic factor, for example, an anti-VEGF neutralizing monoclonal antibody (Borgstrom et al., supra, 1999). An anti-angiogenic agent also can inhibit another angiogenic factor such as a member of the fibroblast growth factor family such as FGF-1 (acidic), FGF-2 (basic), FGF-4 or FGF-5 (Slavin et al., Cell Biol. Int. 19:431-444 (1995); Folkman and Shing, J. Biol. Chem. 267:10931-10934 (1992)) or an angiogenic factor such as angiopoietin-1, a factor that signals through the endothelial cell-specific Tie2 receptor tyrosine kinase (Davis et al., Cell 87:1161-1169 (1996); and Suri et al., Cell 87:1171-1180 (1996)), or the receptor of one of these angiogenic factors. It is understood that a variety of mechanisms can act to inhibit activity of an angiogenic factor including, without limitation, direct inhibition of receptor binding, indirect inhibition by reducing secretion of the angiogenic factor into the extracellular space, or inhibition of expression, function or signaling of the angiogenic factor.

A variety of other molecules also can function as anti-angiogenic agents including, without limitation, angiostatin; a kringle peptide of angiostatin; endostatin; anastellin, heparin-binding fragments of fibronectin; modified forms of antithrombin; collagenase inhibitors; basement membrane turnover inhibitors; angiostatic steroids; platelet factor 4 and fragments and peptides thereof; thrombospondin and fragments and peptides thereof; and doxorubicin (O'Reilly et al., Cell 79:315-328 (1994)); O'Reilly et al., Cell 88:277-285 (1997); Homandberg et al., Am. J. Path. 120:327-332 (1985); Homandberg et-al., Biochim. Biophys. Acta 874:61-71 (1986); and O'Reilly et al., Science 285:1926-1928 (1999)). Commercially available anti-angiogenic agents include, for example, angiostatin, endostatin, metastatin and 2ME2 (EntreMed; Rockville, Md.); anti-VEGF antibodies such as Avastin (Genentech; South San Francisco, Calif.); and VEGFR-2 inhibitors such as SU5416, a small molecule inhibitor of VEGFR-2 (SUGEN; South San Francisco, Calif.) and SU6668 (SUGEN), a small molecule inhibitor of VEGFR-2, platelet derived growth factor and fibroblast growth factor I receptor. It is understood that these and other anti-angiogenic agents can be prepared by routine methods and are encompassed by the term "anti-angiogenic agent" as used herein.

The conjugates disclosed herein can also be used to treat wounds or tissue injuries, or sites where clots form. Moieties useful for this purpose can include molecules belonging to several basic groups including anti-inflammatory agents which prevent inflammation, restenosis preventing drugs which prevent tissue growth, anti-thrombogenic drugs which inhibit or control formation of thrombus or thrombolytics, and bioactive agents which regulate tissue growth and enhance healing of the tissue. Examples of active agents include but are not limited to steroids, fibronectin, anti-clotting drugs, anti-platelet function drugs, drugs which prevent smooth muscle cell growth on inner surface wall of vessel, heparin, heparin fragments, aspirin, coumadin, tissue plasminogen activator (TPA), urokinase, hirudin, streptokinase, antiproliferatives (methotrexate, cisplatin, fluorouracil, Adriamycin), antioxidants (ascorbic acid, beta carotene, vitamin E), antimetabolites, thromboxane inhibitors, non-steroidal and steroidal anti-inflammatory drugs, beta and calcium channel blockers, genetic materials including DNA and RNA fragments, complete expression genes, antibodies, lymphokines, growth factors, prostaglandins, leukotrienes, laminin, elastin, collagen, and integrins.

Useful therapeutic agents also can be antimicrobial peptides. This can be particularly useful for targeting a wound or other infected sites. Thus, also disclosed are conjugates in which a homing molecule that selectively homes to tumor stroma, wounds, or plasma clots and interacts with fibrin-fibronectin is linked to an antimicrobial peptide, where the conjugate is selectively internalized and exhibits a high toxicity to the targeted area, and where the antimicrobial peptide has low mammalian cell toxicity when not linked to the homing molecule. As used herein, the term "antimicrobial peptide" means a naturally occurring or synthetic peptide having antimicrobial activity, which is the ability to kill or slow the growth of one or more microbes and which has low mammalian cell toxicity when not linked to a homing molecule. An antimicrobial peptide can, for example, kill or slow the growth of one or more strains of bacteria including a Gram-positive or Gram-negative bacteria, or a fungi or protozoa. Thus, an antimicrobial peptide can have, for example, bacteriostatic or bacteriocidal activity against, for example, one or more strains of Escherichia coli, Pseudomonas aeruginosa or Staphylococcus aureus. While not wishing to be bound by the following, an antimicrobial peptide can have biological activity due to the ability to form ion channels through membrane bilayers as a consequence of self-aggregation.

An antimicrobial peptide is typically highly basic and can have a linear or cyclic structure. As discussed further below, an antimicrobial peptide can have an amphipathic .alpha.-helical structure (see U.S. Pat. No. 5,789,542; Javadpour et al., J. Med. Chem. 39:3107-3113 (1996); and Blondelle and Houghten, Biochem. 31: 12688-12694 (1992)). An antimicrobial peptide also can be, for example, a β-strand/sheet-forming peptide as described in Mancheno et al., J. Peptide Res. 51:142-148 (1998).

An antimicrobial peptide can be a naturally occurring or synthetic peptide. Naturally occurring antimicrobial peptides have been isolated from biological sources such as bacteria, insects, amphibians, and mammals and are thought to represent inducible defense proteins that can protect the host organism from bacterial infection. Naturally occurring antimicrobial peptides include the gramicidins, magainins, mellitins, defensins and cecropins (see, for example, Maloy and Kari, Biopolymers 37:105-122 (1995); Alvarez-Bravo et al., Biochem. J. 302:535-538 (1994); Bessalle et al., FEBS 274:-151-155 (1990.); and Blondelle and Houghten in Bristol (Ed.), Annual Reports in Medicinal Chemistry pages 159-168 Academic Press, San Diego). An antimicrobial peptide also can be an analog of a natural peptide, especially one that retains or enhances amphipathicity (see below).

An antimicrobial peptide incorporated into a conjugate can have low mammalian cell toxicity when not linked to a tumor homing molecule. Mammalian cell toxicity readily can be assessed using routine assays. As an example, mammalian cell toxicity can be assayed by lysis of human erythrocytes in vitro as described in Javadpour et al., supra, 1996. An antimicrobial peptide having low mammalian cell toxicity is not lytic to human erythrocytes or requires concentrations of greater than 100 µM for lytic activity, preferably concentrations greater than 200, 300, 500 or 1000 µM.

In one embodiment, disclosed are conjugates in which the antimicrobial peptide portion promotes disruption of mitochondrial membranes when internalized by eukaryotic cells. In particular, such an antimicrobial peptide preferentially disrupts mitochondrial membranes as compared to eukaryotic membranes. Mitochondrial membranes, like bacterial membranes but in contrast to eukaryotic plasma membranes, have a high content of negatively charged phospholipids. An antimicrobial peptide can be assayed for activity in disrupting mitochondrial membranes using, for example, an assay for mitochondrial swelling or another assay well known in the art. $_D$(KLAKLAK)$_2$, (SEQ ID NO: 8) for example, is an antimicrobial peptide which induces marked mitochondrial swelling at a concentration of 10 µM, significantly less than the concentration required to kill eukaryotic cells.

An antimicrobial peptide that induces significant mitochondrial swelling at, for example, 50 µM, 40 µ.M, 30 µM, 20 µM, 10 µM, or less, is considered a peptide that promotes disruption of mitochondrial membranes.

An antimicrobial peptide can include, for example, the sequence (KLAKLAK)$_2$ (SEQ ID NO: 9), (KLAKKLA)$_2$ (SEQ ID NO: 10), (KAAKKAA)$_2$ (SEQ ID NO: 11), or (KLGKKLG)$_3$ (SEQ ID NO: 12), and, in one embodiment, includes the sequence $_D$(KLAKLAK)$_2$ (SEQ ID NO: 8).

Antimicrobial peptides generally have random coil conformations in dilute aqueous solutions, yet high levels of helicity can be induced by helix-promoting solvents and amphipathic media such as micelles, synthetic bilayers or cell membranes. α-Helical structures are well known in the art, with an ideal α-helix characterized by having 3.6 residues per turn and a translation of 1.5 Å per residue (5.4 Å per turn; see Creighton, Proteins: Structures and Molecular Properties W. H Freeman, New York (1984)). In an amphipathic α-helical structure, polar and non-polar amino acid residues are aligned into an amphipathic helix, which is an α-helix in which the hydrophobic amino acid residues are predominantly on one face, with hydrophilic residues predominantly on the opposite face when the peptide is viewed along the helical axis.

Antimicrobial peptides of widely varying sequence have been isolated, sharing an amphipathic α-helical structure as a common feature (Saberwal et al., Biochim. Biophys. Acta 1197:109-131 (1994)). Analogs of native peptides with amino acid substitutions predicted to enhance amphipathicity and helicity typically have increased antimicrobial activity. In general, analogs with increased antimicrobial activity also have increased cytotoxicity against mammalian cells (Maloy et al., Biopolymers 37:105-122 (1995)).

As used herein in reference to an antimicrobial peptide, the term "amphipathic α-helical structure" means an α-helix with a hydrophilic face containing several polar residues at physiological pH and a hydrophobic face containing nonpolar residues. A polar residue can be, for example, a lysine or arginine residue, while a nonpolar residue can be, for example, a leucine or alanine residue. An antimicrobial peptide having an amphipathic .alpha.-helical structure generally has an equivalent number of polar and nonpolar residues within the amphipathic domain and a sufficient number of basic residues to give the peptide an overall positive charge at neutral pH (Saberwal et al., Biochim. Biophys. Acta 1197:109-131 (1994)). One skilled in the art understands that helix-promoting amino acids such as leucine and alanine can be advantageously included in an antimicrobial peptide (see, for example, Creighton, supra, 1984). Synthetic, antimicrobial peptides having an amphipathic α-helical structure are known in the art, for example, as described in U.S. Pat. No. 5,789,542 to McLaughlin and Becker.

It is understood by one skilled in the art of medicinal oncology that these and other agents are useful therapeutic agents, which can be used separately or together in the disclosed conjugates and methods. Thus, it is understood that a conjugate can contain one or more of such therapeutic agents and that additional components can be included as part of the conjugate, if desired. As a non-limiting example, it can be desirable in some cases to utilize an oligopeptide spacer between the homing molecule and the therapeutic agent (Fitzpatrick and Garnett, Anticancer Drug Des. 10:1-9 (1995)).

Other useful agents include thrombolytics, aspirin, anticoagulants, painkillers and tranquilizers, beta-blockers, ace-inhibitors, nitrates, rhythm-stabilizing drugs, and diuretics. Agents that limit damage to the heart work only if given within a few hours of the heart attack. Thrombolytic agents that break up blood clots and enable oxygen-rich blood to flow through the blocked artery increase the patient's chance of survival if given as soon as possible after the heart attack. Thrombolytics given within a few hours after a heart attack are the most effective. Injected intravenously, these include anisoylated plasminogen streptokinase activator complex (APSAC) or anistreplase, recombinant tissue-type plasminogen activator (r-tPA), and streptokinase. The disclosed conjugates can use any of these or similar agents.

2. Detectable Agents

The moiety in the disclosed conjugates can also be a detectable agent. A variety of detectable agents are useful in the disclosed methods. As used herein, the term "detectable agent" refers to any molecule which can be detected. Useful detectable agents include moieties that can be administered in vivo and subsequently detected. Detectable agents useful in the disclosed conjugates and imaging methods include yet are not limited to radiolabels and fluorescent molecules. The detectable agent can be, for example, any moiety that facilitates detection, either directly or indirectly, preferably by a non-invasive and/or in vivo visualization technique. For example, a detectable agent can be detectable by any known imaging techniques, including, for example, a radiological technique. Detectable agents can include, for example, a contrasting agent, e.g., where the contrasting agent is ionic or non-ionic. In some embodiments, for instance, the detectable agent comprises a tantalum compound and/or a barium compound, e.g., barium sulfate. In some embodiments, the detectable agent comprises iodine, such as radioactive iodine. In some embodiments, for instance, the detectable agent comprises an organic iodo acid, such as iodo carboxylic acid, triiodophenol, iodoform, and/or tetraiodoethylene. In some embodiments, the detectable agent comprises a non-radioactive detectable agent, e.g., a non-radioactive isotope. For example, Gd can be used as a non-radioactive detectable agent in certain embodiments.

Other examples of detectable agents include moieties which emit or can be caused to emit detectable radiation (e.g., fluorescence excitation, radioactive decay, spin resonance excitation, etc.), moieties which affect local electromagnetic fields (e.g., magnetic, ferromagnetic, ferrimagnetic, paramagnetic, and/or superparamagnetic species), moieties which absorb or scatter radiation energy (e.g., chromophores and/or fluorophores), quantum dots, heavy elements and/or compounds thereof. See, e.g., detectable agents described in U.S. Publication No. 2004/0009122. Other examples of detectable agents include a proton-emitting moiety, a radiopaque moiety, and/or a radioactive moiety, such as a radionuclide like Tc-99m and/or Xe-13. Such moieties can be used as a radiopharmaceutical. In still other embodiments, the disclosed compositions can comprise one or more different types of detectable agents, including any combination of the detectable agents disclosed herein.

Useful fluorescent moieties include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazins, phycoerythrin, macrocyclic chelates of lanthanide ions such as quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 OLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Particularly useful fluorescent labels include fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm: 568 nm), Cy3.5 (581 nm: 588 mm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio. Fluorescent probes and there use are also described in Handbook of Fluorescent Probes and Research Products by Richard P. Haugland.

Further examples of radioactive detectable agents include gamma emitters, e.g., the gamma emitters In-111, I-125 and I-131, Rhenium-186 and 188, and Br-77 (see. e.g., Thakur, M. L. et al., Throm Res. Vol. 9 pg. 345 (1976); Powers et al., Neurology Vol. 32 pg. 938 (1982); and U.S. Pat. No. 5,011,686); positron emitters, such as Cu-64, C-11, and O-15, as well as Co-57, Cu-67, Ga-67, Ga-68, Ru-97, Tc-99m, In-113m, Hg-197, Au-198, and Pb-203. Other radioactive detectable agents can include, for example tritium, C-14 and/or thallium, as well as Rh-105, I-123, Nd-147, Pm-151, Sm-153, Gd-159, Tb-161, Er-171 and/or Tl-201.

The use of Technitium-99m (Tc-99m) is preferable and has been described in other applications, for example, see U.S. Pat. Nos. 4,418,052 and 5,024,829. Tc-99m is a gamma emitter with single photon energy of 140 keV and a half-life of about 6 hours, and can readily be obtained from a Mo-99/Tc-99 generator.

In some embodiments, compositions comprising a radioactive detectable agent can be prepared by coupling a targeting moiety with radioisotopes suitable for detection. Coupling can occur via a chelating agent such as diethylenetriaminepentaacetic acid (DTPA), 4,7,10-tetraazacyclododecane-N-,N',N'',N'''-tetraacetic acid (DOTA) and/or metallothionein, any of which can be covalently attached to the targeting moiety. In some embodiments, an aqueous mixture of technetium-99m, a reducing agent, and a water-soluble ligand can be prepared and then allowed to react with a disclosed targeting moiety. Such methods are known in the art, see e.g., International Publication No. WO 99/64446. In some embodiments, compositions comprising radioactive iodine, can be prepared using an exchange reaction. For example, exchange of hot iodine for cold iodine is well known in the art. Alternatively, a radio-iodine labeled compound can be prepared from the corresponding bromo compound via a tributylstannyl intermediate.

Magnetic detectable agents include paramagnetic contrasting agents, e.g., gadolinium diethylenetriaminepentaacetic acid, e.g., used with magnetic resonance imaging (MRI) (see, e.g., De Roos, A. et al., Int. J. Card. Imaging Vol. 7 pg. 133 (1991)). Some preferred embodiments use as the detectable agent paramagnetic atoms that are divalent or trivalent ions of elements with an atomic number 21, 22, 23, 24, 25, 26, 27, 28, 29, 42, 44, 58, 59, 60, 61, 62, 63, 64, 65, 66, 67, 68, 69, or 70. Suitable ions include, but are not limited to, chromium(III), manganese(II), iron(II), iron(III), cobalt(II), nickel(II), copper(II), praseodymium(III), neodymium(III), samarium(III) and ytterbium(III), as well as gadolinium(III), terbiurn(III), dysoprosium(III), holmium (III), and erbium(III). Some preferred embodiments use atoms with strong magnetic moments, e.g., gadolinium(III).

In some embodiments, compositions comprising magnetic detectable agents can be prepared by coupling a targeting moiety with a paramagnetic atom. For example, the metal oxide or a metal salt, such as a nitrate, chloride or sulfate salt, of a suitable paramagnetic atom can be dissolved or suspended in a water/alcohol medium, such as methyl, ethyl, and/or isopropyl alcohol. The mixture can be added to a solution of an equimolar amount of the targeting moiety in a similar water/alcohol medium and stirred. The mixture can be heated moderately until the reaction is complete or nearly complete. Insoluble compositions formed can be obtained by filtering, while soluble compositions can be obtained by evaporating the solvent. If acid groups on the chelating moieties remain in the disclosed compositions, inorganic bases (e.g., hydroxides, carbonates and/or bicarbonates of sodium, potassium and/or lithium), organic bases, and/or basic amino acids can be used to neutralize acidic groups, e.g., to facilitate isolation or purification of the composition.

In preferred embodiments, the detectable agent can be coupled to the homing molecule in such a way so as not to interfere with the ability of the homing molecule to home to the target. In some embodiments, the detectable agent can be chemically bound to the homing molecule. In some embodiments, the detectable agent can be chemically bound to a moiety that is itself chemically bound to the homing molecule, indirectly linking the imaging and targeting moieties.

D. Pharmaceutical Compositions and Carriers

The disclosed conjugates can be administered in vivo in a pharmaceutically acceptable carrier. By "pharmaceutically acceptable" is meant a material that is not biologically or otherwise undesirable, i.e., the material can be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. The materials can be in solution, suspension (for example, incorporated into microparticles, liposomes, or cells).

1. Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

E. Combinatorial Chemistry

The disclosed compositions can be used as targets for any combinatorial technique to identify molecules or macromolecular molecules that interact with the disclosed compositions in a desired way. Also disclosed are the compositions that are identified through combinatorial techniques or screening techniques in which the compositions disclosed in SEQ ID NOS: 1 and 2 or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, CLT1 and CLT2, are also disclosed. Thus, the products produced using the combinatorial or screening approaches that involve the disclosed compositions, such as, CLT1 and CLT2, are also considered herein disclosed.

F. Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as, CLT1 and CLT2, are also disclosed. Thus, the products produced using the molecular modeling approaches that involve the disclosed compositions, such as, CLT1 and CLT2 are also considered herein disclosed.

Thus, one way to isolate molecules that bind a molecule of choice is through rational design. This can be achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol._Toxiciol.* 29, 111-122; Perry and Davies, *QSAR: Quantitative Structure—Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

G. Compositions with Similar Functions

It is understood that the compositions disclosed herein have certain functions, such as interacting with the fibrin-fibronectin complex. Disclosed herein are certain structural requirements for performing the disclosed functions, and it is understood that there are a variety of structures which can perform the same function which are related to the disclosed structures, and that these structures will ultimately achieve the same result, for example stimulation or inhibition.

H. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include CLT1 and CLT2.

I. Mixtures

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

J. Systems

Disclosed are systems useful for performing, or aiding in the performance of, the disclosed method. Systems generally comprise combinations of articles of manufacture such as structures, machines, devices, and the like, and compositions, compounds, materials, and the like. Such combinations that are disclosed or that are apparent from the disclosure are contemplated.

K. Computer Readable Media

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

Methods

Disclosed are methods of directing a moiety to tumors, sites of injury, or sites of blood clots in a subject, comprising administering to the subject a conjugate comprising a moiety linked to a fibrin- or fibronectin-binding peptide, or to a peptide that binds clotted plasma protein. In one example, the peptide can comprise the amino acid sequence of SEQ ID NO: 1 or SEQ ID NO: 2, or a related amino acid sequence.

Also disclosed are methods of directing a moiety to tumors, sites of injury, and/or sites of blood clots in a subject, comprising administering to the subject a conjugate, wherein the conjugate comprises a moiety linked to a peptide comprising an amino acid segment comprising the amino acid sequence of SEQ ID NO: 1 or SEQ ID NO: 2, an amino acid sequence at least about 90% identical to the amino acid sequence of SEQ ID NO:1 or SEQ ID NO:2, or the amino acid sequence of SEQ ID NO:1 or SEQ ID NO:2 having one or more conservative amino acid substitutions.

The moiety can be used to detect the cancer, visualize one or more tumors, or both. The subject can have one or more sites of injury, wherein the moiety is directed to one or more of the sites of injury. The conjugate can treat at least one of the sites of injury. The conjugate can have a therapeutic effect on at least one of the sites of injury. The moiety can be used to detect, visualize, or image at least one of the sites of injury, or a combination. The subject can have one or more blood clots, wherein the moiety is directed to one or more of the blood clots. The conjugate can treat at least one of the blood clots. The conjugate can have a therapeutic effect on at least one of the blood clots. The moiety can be used to detect, visualize, or image at least one blood clot.

Also disclosed are methods of directing a moiety to tumors, including tumor stroma, or a plasma clot or sites of injuries or wounds in a subject by administering to the subject a conjugate which contains the moiety linked to a homing molecule that selectively homes to tumors, including tumor stroma, or a plasma clot or sites of injuries or wounds, thereby directing the moiety to tumors, including tumor stroma, or a plasma clot or sites of injuries or wounds.

Disclosed herein is a method of directing a moiety to fibrin-fibronectin complex in clots in a subject, comprising administering to the subject a conjugate as disclosed herein. The moiety can be directed to tumor stroma in the subject in one embodiment, and the conjugate can treat cancer, or have a therapeutic effect on the cancer. In one example, the tumor size can be reduced. The growth of a tumor can be reduced, stopped or reversed.

Also disclosed are methods of reducing the number of tumor vessels in a subject by administering to the subject a conjugate which includes a therapeutic agent linked to a homing molecule that selectively homes to tumors, including tumor stroma, thereby reducing the number of tumor vessels in the subject. The disclosed method can be useful, for example, for reducing the number of breast tumor vessels. In a method for reducing the number of tumor vessels, a variety of therapeutic agents can be incorporated into the conjugate administered to the subject, including, for example, cancer chemotherapeutic agents, cytotoxic agents, and anti-angiogenic agents.

Also provided herein is a method of treating cancer in a subject by administering to the subject a conjugate which contains a therapeutic agent linked to a homing molecule that selectively homes to tumors, including tumor stroma. As a non-limiting example, the disclosed method can be useful for treating breast cancer.

The disclosed compositions can be used to treat any disease where uncontrolled cellular proliferation occurs such as cancers. A non-limiting list of different types of cancers can be as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumours, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

Exemplified herein is a homing molecule which selectively homes to the matrix of breast tumor stroma but which does not detectably home to non-tumor tissue such as brain, heart, kidney, lung, pancreatic and breast tissue. Additional homing molecules that, like SEQ ID NO: 1 and SEQ ID NO: 2, selectively homes to tumor stroma or plasma clots, can be identified using in vivo panning as described in U.S. Pat. No. 5,622,699 coupled, if desired, with ex viva selection or can be identified through in vitro assays such as the ability to interact with fibrin-fibronectin as disclosed herein in the Example.

The compositions can be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

Also disclosed is a method of imaging clotted plasma in a subject by administering to the subject a conjugate containing a detectable agent linked to a homing molecule that selectively homes to plasma clots; and detecting the conjugate, thereby imaging the area of interest.

The disclosed methods for imaging plasma clots can be useful for detecting the presence of tumor stroma associated with a variety of tumors, including breast, ovarian, brain, colon, kidney, lung, bladder and prostate tumors and melanomas. Following administration of a conjugate containing a detectable agent, tumor stroma can be visualized. If the image is positive for the presence of tumor blood vessels, the tumor can be evaluated for size and quantity of infiltration. These results provide valuable information to the clinician with regard to the stage of development of the cancer and the presence or probability of metastasis.

In a method of imaging tumor stroma, the conjugate administered contains a detectable agent that allows detection or visualization of tumor tissue in and around tumors, for example in and around breast tumors. For in vivo diagnostic imaging of tumor stroma, a homing molecule can be linked to a detectable agent that, upon administration to the subject, is detectable external to the subject. Such a detectable agent can be, for example, a gamma ray emitting radionuclide such as indium-113, indium-115 or technetium-99; following administration to a subject, the conjugate can be visualized using a solid scintillation detector.

Also disclosed are methods of identifying a tumor homing molecule that selectively homes to tumor stroma by contacting a substantially purified stroma sample or fragment thereof, with one or more molecules; and determining specific binding of a molecule to the substantially purified stroma or fragment thereof, where the presence of specific binding identifies the molecule as a tumor homing molecule that selectively homes to tumor stroma. The disclosed method can further include, if desired, the steps of administering the fibrin-fibronectin interacting molecule in vivo; and determining interaction of the molecule with tumor stroma. If desired, the substantially purified stroma sample can be immobilized on a support.

The compositions disclosed herein and the compositions necessary to perform the disclosed methods can be made using any method known to those of skill in the art for that particular reagent or compound unless otherwise specifically noted.

One method of producing the disclosed proteins, such as SEQ ID NOs: 1 and 2, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant GA (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

EXAMPLE

The following example is put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A. Peptides Selected from Plasma Clot Bind to Tumor Stroma

The phage selection scheme was designed to amplify phage that bind to plasma clots but not to anti-coagulated plasma. Three rounds of selection produced a pool with 7-fold increased binding to plasma clots. Additional selection rounds did not increase the binding. Sequencing showed that the phage encoding the peptide insert CGLIIQKNEC (CLT1 peptide, SEQ ID NO: 1) and CNAGESSKNC (CLT2 peptide, SEQ ID NO: 2) were highly enriched among the clot binding phage. Three out of 24 clones sequenced encoded CLT1, while two encoded CLT2; the rest of the clones were only represented once. The CLT phage clones bound to plasma clots with 3 to 4-fold efficiency compared to control phage. They did not significantly bind to clots made out of purified fibrin, or fibronectin immobilized on plastic.

To determine whether the CLT peptides would recognize clotted plasma proteins in vivo, the peptides were synthesized as fluorescein conjugates and imaged their accumulation in tumors. Mice bearing orthotopic MDA-MB-435 xenograft tumors were intravenously injected with fluorescein-conjugated CLT1 (n=6), CLT2 (n=4), or a control peptide (n=4) with the sequence KAREC (SEQ ID NO: 5). Examination of whole tissues from these mice under blue light 3 hours after the peptide injection revealed intense fluorescence in the tumors of the mice injected with CLT1 and CLT2, whereas essentially no fluorescence was detected in tumors from the control peptide-injected mice (FIG. 1). No fluorescence was detected in healthy organs of the CLT-injected animals.

Figure 1M:
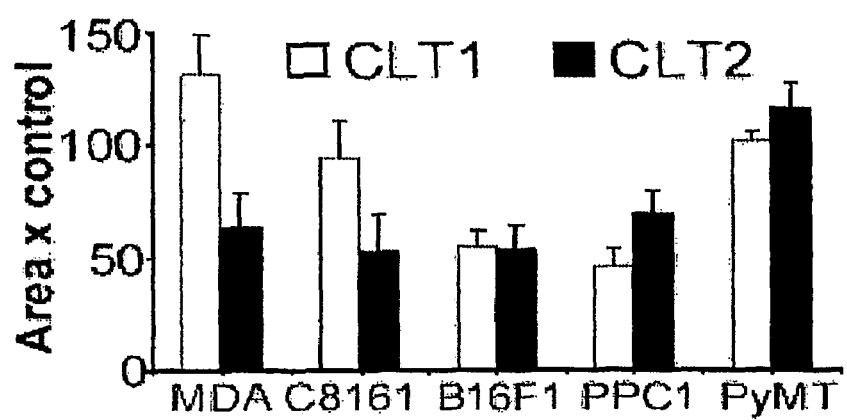
Figure 2:
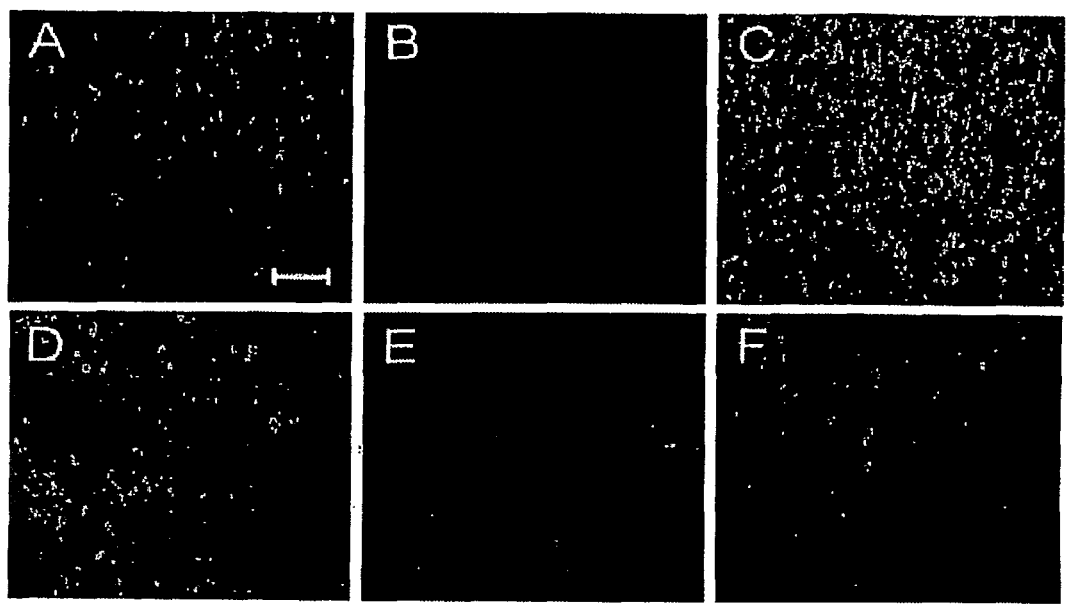
FIGS. 2A to 2F show a peptide overlay assay, and that CLT peptide binds to clinical human tumors. Frozen sections of mouse Lewis Lung carcinoma were incubated with fluorescein-conjugated CLT1 peptide, washed, and analyzed for fluorescence. The fibrillar network produced by the peptide (A) was eliminated by co-incubation with unlabeled CLT peptide (B) but not by a control peptide (C). Two human clinical breast cancers (D and E), and PPC1 xenograft tumor (F) were also recognized by the CLT peptide. Scale bar 50 µm (all panels).

Upon histological examination, CLT peptide fluorescence in tumors appeared in a network pattern within the tumors (FIG. 1C, G). Tumor homing of both peptides was strongly reduced after co-injection of fluorescein-conjugated CLT1 and CLT2 in combination with unlabeled CLT2 in 5 fold excess (FIG. 1D, H). This indicates that the CLT1 peptide recognizes the same binding site within the tumor as CLT2. Quantification of these results showed that the intensity of fluorescence in the MDA-MB-435 tumors of mice injected with the CLT peptides was 60 to 130 times stronger than in mice injected with the KAREC (SEQ ID NO: 5) control peptide (FIG. 1M). Also shown in FIG. 1M is that the CLT peptides specifically accumulated in all of the various tumors tested (n=2-8). A fibrillar pattern similar to the one shown in FIGS. 1C and 1G was seen in each of these other tumors. To study the ability of the CLT peptides to recognize human clinical cancers, a peptide overlay assay was developed. Overlay with the CLT1 peptide produced a fibrillar network in mouse Lewis lung carcinoma similar to that seen in the tumors after i.v. injection of the peptide (FIG. 2A). The binding of the peptide was also inhibited by unlabeled CLT1 peptide (FIG. 2B) but not by a control peptide (FIG. 2 C), showing the specificity of the binding. Sections from two clinical breast cancers (FIG. 2D, E) and from PPC1 xenografts were positive in this overlay assay (FIG. 2F).

B. CLT Peptides Associate with Fibrin and Fibronectin in Tumor Stroma

Figures 3A, 3B, 3C, 3D, 3E, 3F, 3G:
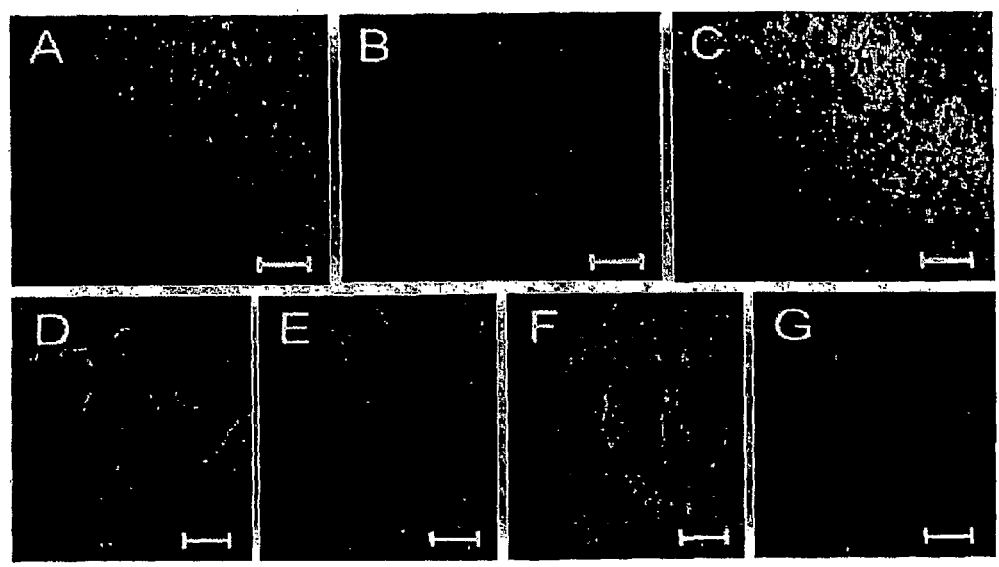
FIGS. 3A to 3H show CLT peptides associate with fibrin and fibronectin in tumor stroma and require a fibrin/fibronectin matrix for tumor homing. Frozen sections of MDA-MB-435 xenograft tumors from mice injected with fluorescein-conjugated CLT1 were stained for fibrin(ogen). The peptide fluorescence (A) and fibrin staining (B) show similar patterns with overlapping distribution (C). Intravenously injected CLT peptides (CLT1 is shown) produce a fluorescent meshwork in B16F1 tumors grown in C57BL/6 mice (FIG. 3D), but not in tumors grown in fibrinogen knockout mice (FIG. 3E). CLT1 also homes to B16F1 tumors in wild type littermates of plasma fibronectin-deficient C57BL/6-Fn(fl/fl) Mx-Cre$^+$ mice (F), but tumors of mice deficient in plasma fibronectin were negative (G). The micrographs show representative images; panel H summarizes and quantifies the results. WT, wild type mice; FG-, fibrinogen knockout mice; FN-, plasma fibronectin deficient mice. Error bars show mean±SEM, scale bars 50 µm.

Staining of tumor sections with antibodies against fibrin (ogen) produces a fibrillar staining that is not seen in normal tissues (Dvorak, H. F., Senger, D. R., Dvorak, A. M., Harvey, V. S., & McDonagh, J. (1985) Science, 227, 1059-61). Fluorescence from intravenously injected CLT peptide (CLT1; FIG. 3A) and fibrin staining (FIG. 3B) co-localized (FIG. 3C) in tumor sections of MDA-MB-435 breast cancer xenografts. Plasma fibronectin and fibrin are deposited together into plasma clots by Factor XIII activity (Mosher, D. F. (1975) J. Biol. Chem., 250, 6614-21). The relationship of CLT peptide fluorescence and fibronectin staining in tumors was then analyzed. The results showed that CLT peptides also co-distribute with fibronectin. The distribution of the CLT peptides, fibrin, and fibronectin in MMTV-PyMT transgenic breast tumors was also studied. The results were identical to those obtained with the MDA-MB-435 xenografts.

C. CLT Peptide Tumor Homing Requires Fibrin and Plasma Fibronectin

Figure 3H:
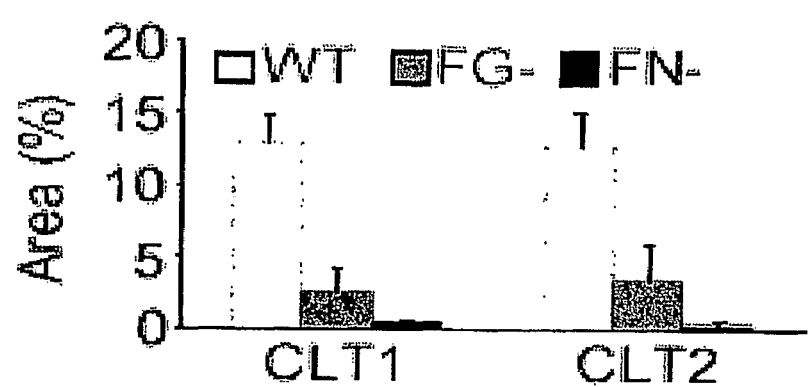

Knockout mice were employed to study the role of fibrin(ogen) and fibronectin in the homing of the CLT peptides to tumors. Fibrinogen knockout mice are viable (Palumbo, J. S., Kombrinck, K. W., Drew, A. F., Grimes, T. S., Kiser, J. H. Jay L. Degen, J. L. & Bugge, T. H. (2000), Blood 96, 3302-3309) and were used as tumor recipients. Complete absence of fibronectin is lethal, but mice that lack plasma fibronectin can be generated by postnatally deleting the fibronectin gene in the liver (Sakai, T., Johnson, K. J., Murozono, M., Sakai, K., Magnuson, M. A., Wieloch, T., Cronberg, T., Isshiki, A., Erickson, H. P., & Fassler R. (2001) Nat. Med. 7, 324-30). The CLT peptides homed to B16F1 tumors grown in wild type C57BL/6 mice (n=10) producing a fibrillar meshwork (CLT1; FIG. 3D). In contrast, only faint, evenly distributed fluorescence was present in tumors (n=4) grown in the fibrinogen knockout mice (which lack the ability to produce fibrin) (FIG. 3E). B16F1 tumors grown in wild type littermates of plasma fibronectin-deficient mice also accumulated CLT peptides in a fibrillar matrix (FIG. 3F), but mice lacking plasma fibronectin (n=6) did not (FIG. 3G). Unlike in the fibrinogen knockout mice, there was no residual peptide binding to the tumors in the plasma fibronectin-deficient mice (FIG. 3H). These results show that both fibrin and fibronectin from plasma are needed for the CLT peptides to highlight a fibrillar matrix in tumors, but that some diffuse binding of the peptide persists in the absence of fibrin.

D. CLT Binds Sites of Tissue Injury In Vivo

Figures 4A, 4B, 4C, 4D, 4E, 4F, 4G:
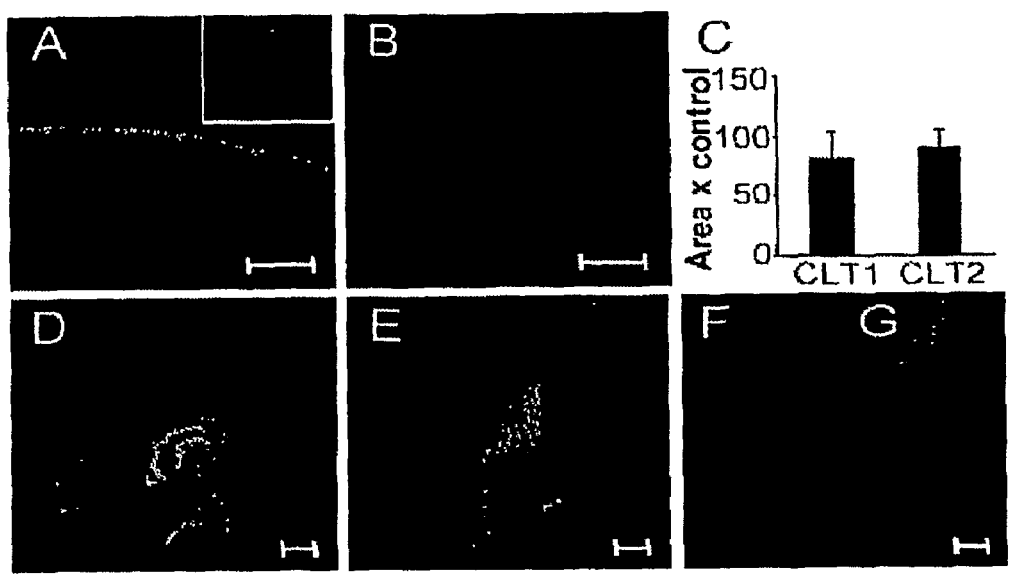
FIGS. 4A to 4G show CLT peptides home to injured tissues. Fluorescent CLT peptide or control peptide was intravenously injected into mice with previously inflicted tissue injury. Fluorescein-conjugated CLT2 homes to mouse femoral artery injured with a wire 30 min earlier (panel A and inset) but not to a normal femoral artery (B). Panel C shows quantification of the results for both CLT peptides in the arterial injury model. Muscle crush injury (D) and skin incision (E) made 48 hours earlier also accumulate CLT2. Normal muscle and skin are negative (F and G). Scale bars 50 µm.
Figure 5:
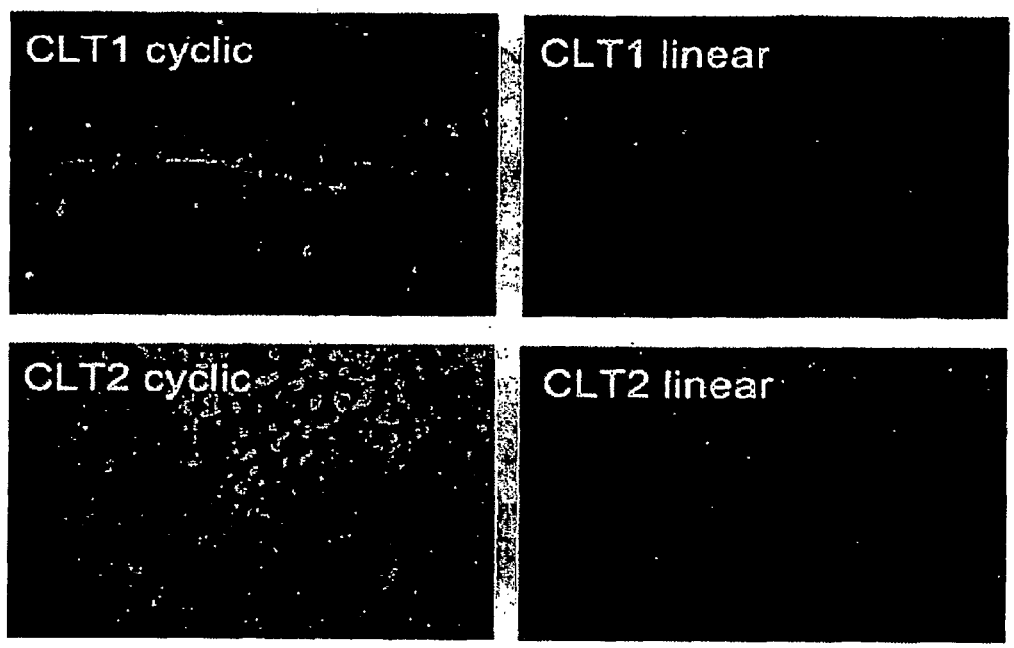
FIG. 5 shows the results of CLT peptide cyclization. Mice bearing orthotopic MDA-MB-435 xenograft tumors were intravenously injected with fluorescein-conjugated CLT1 and 2 (500 µg). After 3 h, the mice were perfused with PBS and 4% paraformaldehyde. Histological analysis showed that only the cyclic versions of the CLT peptides accumulated in the tumor tissue.
Figure 6:
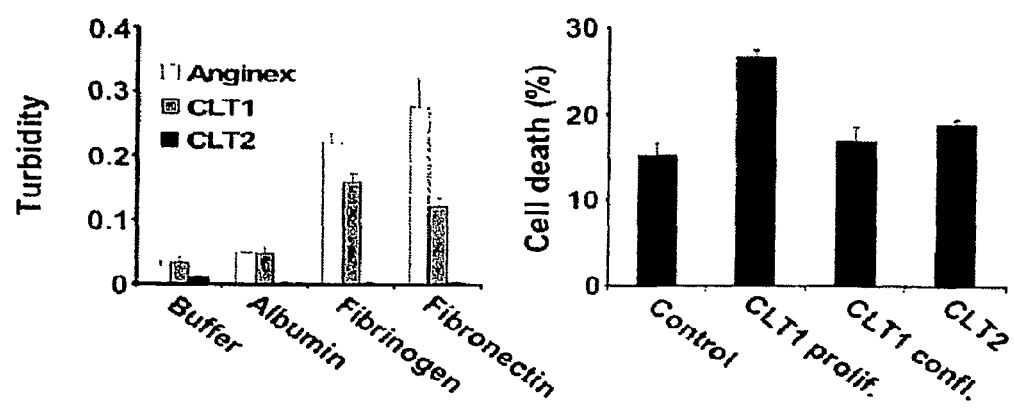
FIG. 6 shows CLT1 is amyloidogenic for plasma proteins and cytotoxic for endothelial cells. CLT1 contains a sequence of three consecutive hydrophobic residues, LII (leucine-isoleucine-isoleucine). This motif is very similar to the VII sequence (V, valine) which causes proteins to form large insoluble aggregates (Esteras-Chopo et al. 2005). The ability of CLT1 to form aggregates with the plasma proteins fibronectin and fibrinogen was demonstrated in vitro by measuring light scattering at 600 nm (turbidity). CLT1 was not amyloidogenic when it was added to an albumin solution. The angiogenesis inhibitor Anginex which has been reported to form aggregates in the presence of fibronectin and fibrinogen, was used as a positive control (Akerman, Pilch et al. 2005). The ability of CLT1 to aggregate proteins correlates with its cytotoxicity for human umbilical venous endothelial cells (HUVECs). CLT1 added to the culture media at 150 µg/ml induced cell death within 24 h only in proliferating but not in confluent HUVECs. CLT2 (CNA-GESSKNEC, SEQ ID NO: 22) was neither amyloidogenic nor cytotoxic.

Clotting is an important part of wound healing. Therefore, CLT peptide homing to tissue injuries was tested. Fluorescein-conjugated CLT peptides homed to de-endothelialized femoral arteries (n=5), producing strong fluorescence in the vessel wall (FIG. 4A). CLT homing was also seen in crush injuries of the muscle (n=3; FIG. 4D) and in skin wounds resulting from incisions (n=4; FIG. 4E). No CLT peptide homing was observed in intact arteries, muscles, skin (FIG. 4B, F, G) or other healthy tissues of the mice with the injuries, and a control peptide showed no homing to the injured tissues.

E. Material and Methods

1. Animals, Cell Lines, and Tissues

B16F1 mouse melanoma, Lewis lung carcinoma, C8161 human melanoma, MDA-MB-435 human breast cancer, and PPC-1 human prostate cancer cells (American Type Culture Collection) were maintained in RPMI or DMEM supplemented with 10% FCS. Human tumor cells ($1 \times 10^6$) were injected into the mammary fat pad or the flank of nude BALB/c nu/nu mice to induce tumors. MMTV PyMT mice were provided by Dr. Robert Oshima (Burnham Institute for Medical Research, La Jolla, Calif.). The MMTV PyMT mice develop breast cancer under the influence of a polyoma middle T antigen driven by the mouse tumor virus promoter (Siegel, P. M., Ryan, E. D., Cardiff, R. D., Muller W. J. (1999) EMBO J., 18, 2149-64). B16F1 tumors induced by injecting $1 \times 10^6$ cells subcutaneously were grown in the flank of fibrinogen knock-out mice (Suh, T. T., Holmback, K., Jensen, N. J., Daugherty, C. C., Small, K., Simon, D. I., Potter, S., & Degen, J. L. (1995) Genes Dev. 9, 2020-2033), and of transgenic plasma fibronectin-deficient C57BL/6-Fn (fl/fl) Mx-Cre+ (Sakai, T., Johnson, K. J., Murozono, M., Sakai, K., Magnuson, M. A., Wieloch, T., Cronberg, T., Isshiki, A., Erickson, H. P., & Fassler R. (2001) Nat. Med. 7, 324-30) and their wild type littermates. Deletion of the fibronectin gene in the liver was induced by poly(I):poly(C) (Yi, M., Sakai, T., Fassler, R., & Ruoslahti, E. (2003) Proc. Natl. Acad. Sci. USA. 100, 11435-11438). Frozen human tissues from clinical breast cancers were provided by the Western Division of the NCI Cooperative Human Tissue Network (Vanderbilt University Medical Center, Nashville, Tenn.).

2. Phage Library

A cyclic peptide library with the general structure of CX8C (C=cysteine; X=any amino acid) was designed to express 5-15 peptide copies on a T7 10-3b phage vector (T7 Select Kit, Novagen). CX8C encoding oligonucleotides were synthesized with flanking EcoRI/HindIII adapters (N=any nucleotide, K=guanine or thymine, M=adenine or cytosine):

```
                                          (SEQ ID NO: 6)
5'-AATTCCTGCNNKNNKNNKNNKNNKNNKNNKNNKTGCTA-3'
and
                                          (SEQ ID NO: 7)
3'-GGACGNNMNNMNNMNNMNNMNNMNNMNNMACGATTCGA-5'.
```

The annealed oligonucleotide pairs were ligated to EcoRI/HindIII-digested phage vector according to the T7 Select protocol. The diversity of the peptide library was $5 \times 10^8$ primary recombinants.

3. Clot Formation

Blood was anti-coagulated with 0.4% sodium citrate and centrifuged at 2,500×g. The plasma was collected, spun again to remove remaining blood cells and frozen at −80° C. Clotting was initiated by adding $CaCl_2$ to 20 mM, and the clot was repeatedly washed with PBS.

4. Phage Screening

Human plasma clots were incubated with the CX8C peptide library at 22° C. for 30 min and extensively washed with PBS. Plasma was then added to the clot to remove phage recognizing soluble plasma components. The phage pool that remained bound to the clot was quantified and amplified. The process was repeated until maximum clot binding was reached. The peptide-encoding DNA from 24 randomly picked phage clones in the selected pool was isolated and sequenced.

5. Peptide Synthesis

Peptides were synthesized and conjugated to fluorescein isothiocyanate as described (Laakonen et al. PNAS 2004), and cyclized by exposure to air.

6. Imaging Antibodies and Immunohistology

Imaging under a blue light, and examination of the distribution of fluorescein-conjugated peptides after tail vein injection have been described (Hoffman, R. M. (2005) *Nature Reviews Cancer* 5, 796-806; Laakkonen, P., Akerman, M. E., Biliran, H., Yang, M., Ferrer, F., Karpanen, T., Hoffman, R. M., & Ruoslahti E. (2004) *Proc. Natl. Acad. Sci. USA* 101, 9381-6).

The imaging methods are briefly described as follows: A Leica fluorescence stereomicroscope, model LZ12, equipped with a 50-W mercury lamp, was used for high-magnification imaging. Selective excitation of GFP was produced through a D425y60 band-pass filter and 470 DCXR dichroic mirror. Emitted fluorescence was collected through a long-pass filter GG475 (Chroma Technology, Brattleboro, Vt.) on a Hamamatsu C5810 3-chip cooled color charge-coupled device camera (Hamamatsu Photonics Systems, Bridgewater, N.J.). Images were processed for contrast and brightness and analyzed with the use of IMAGE PRO PLUS 3.1 software (Media Cybernetics, Silver Springs, Md.). Images of 1,024×724 pixels were captured directly on an IBM PC or continuously through video output on a high-resolution Sony VCR model SLV-R1000 (Sony, Tokyo). Imaging at lower magnification that visualized the entire animal was carried out in a light box illuminated by blue light fiber optics (Lightools Research, Encinitas, Calif.) and imaged by using the thermoelectrically cooled color charge-coupled device camera, as described above (Yang, M., Baranov, E., Jiang, P., Sun, F-X., Li, X-M., Li, L., Hasegawa, S., Bouvet, M., Al-Tuwaijri, M., Chishima, T., et al (2000) *Proc. Natl. Acad. Sci. USA* 97, 1206-11).

The mice were perfused through the heart 3 hours after the peptide injection and tissues removed for examination. For fibrin and fibronectin immunostaining, tissues were fixed with 4% paraformaldehyde and stained with biotinylated mouse fibrin(ogen) antiserum (Nordic Immunological Laboratories) or a polyclonal anti-mouse fibronectin (Chemicon), followed by streptavidin Alexa 594 or anti-rabbit Alexa 594 (Molecular Probes), respectively. For peptide overlay, sections of frozen OCT embedded tissue were incubated with 10 µg/ml fluorescein-conjugated peptide for 30 min at room temperature. Tissue fluorescence was quantified using Image-Pro Plus software. At least two images from representative microscopic fields were analyzed from each tissue sample and data from individual mice that received the same treatment (n=2-8) were pooled.

7. Wound Assays

The wire injury of the mouse femoral artery was induced as previously described (Komatsu, M. & Ruoslahti, E. (2005) *Nat Med*. (2005) 11:1346-1350). Thirty minutes after the wire injury, 250 µg of fluorescein-conjugated peptides were injected i.v. Muscle injuries were induced in mice by applying a crush injury to the quadriceps muscle, and 500 µg fluorescein-conjugated peptides were injected i.v. 48 hours later. Skin incisions were studied similarly. The mice were perfused through the heart 4 hours after the peptide injection, and tissues were excised, fixed in 4% paraformaldehyde, and embedded in OCT.

REFERENCES

1. Bissell, M. J., & Radisky, D. (2001) *Nat. Rev. Cancer* 1, 46-54.
2. Kalluri, R. (2003) *Nat. Rev. Cancer* 3, 422-33.
3. Ventimiglia, J. B., Wikstrand, C. J., Ostrowski, L. E., Bourdon, M. A., Lightner, V. A., & Bigner, D. D. (1992) *J. Neuroimmunol*. 36, 41-55.
4. Neri, D., Carnemolla, B., Nissim, A., Leprini, A., Querze, G., Balza, E., Pini, A., Tarli, L., Halin, C., Neri, P., et al. (1997) *Nat. Biotech*. 15, 1271-5.
5. St. Croix, B., Rago, C., Velculescu, V., Traverso, G., Romans, K. E., Montgomery, E., Lal, A., Riggins, G. J., Lengauer, C., Vogelstein, B., et al. (2000) *Science*, 289, 1197-202.
6. Halin, C., Rondini, S., Nilsson, F., Berndt, A., Kosmehl, H., Zardi, L., & Neri, D. (2002) *Nat. Biotechnol*. 20, 264-269.
7. Senger, D. R., Galli, S. J., Dvorak, A. M., Perruzzi, C. A., Harvey, V. S., & H. F. Dvorak. *Science* (1983) 219, 983-985.
8. Dvorak, H. F., Senger, D. R., Dvorak, A. M., Harvey, V. S., & McDonagh, J. (1985) *Science*, 227, 1059-61.
9. Abe, K., Shoji, M., Chen, J., Bierhaus, A., Danave, I., Micko, C., Casper, K., Dillehay, D. L., Nawroth, P. P., & Rickles, F. R. (1999) *Proc. Natl. Acad. Sci. USA* 96, 8663-8.
10. Ruoslahti, E. (2002) *Nat. Rev. Cancer* 2, 83-90.
11. Ellerby, H. M., Wadih, A., Ellerby, L. M., Kane R., Andrusiak R., Del Rio, G., Krajewski, S., Lombardo C. R., Rao, R., & Ruoslahti, E. et al. (1999) *Nature Medicine* 5, 1032-1038.
12. Akerman, M. E., Warren C. W. Chan, W. C. W., Laakkonen, P., Bhatia, S. N., & Ruoslahti E. (2002) *Proc. Natl. Acad. Sci*. 99, 12617-12621.
13. Mosher, D. F. (1975) *J. Biol. Chem.*, 250, 6614-21.
14. Palumbo, J. S., Kombrinck, K. W., Drew, A. F., Grimes, T. S., Kiser, J. H. Jay L. Degen, J. L. & Bugge, T. H. (2000), *Blood* 96, 3302-3309.
15. Sakai, T., Johnson, K. J., Murozono, M., Sakai, K., Magnuson, M. A., Wieloch, T., Cronberg, T., Isshiki, A., Erickson, H. P., & Fassler R. (2001) *Nat. Med*. 7, 324-30.
16. Ten Cate H., Bauer K A., Levi M., Edgington T S., Sublett R D., Barzegar S., Kass B L. & Rosenberg R D. (1993) *J. Clin. Inv*. 92, 1207-12.
17. Morla, A., Ruoslahti, E. (1992) *J. Cell. Biol*. 118, 421-9.
18. Baneyx, G., Baugh, L., & Vogel, V. (2001) *Proc. Natl. Acad. Sci. USA* 98, 14464-8.
19. Flacke, S., Fischer, S., Scott, M. J., Fuhrhop, R. J., Allen, J. S., McLean, M., Winter, P., Sicard, G. A., Gaffney, P. J., Wickline, S. A., et al. (2001) *Circulation* 104, 1280-5.
20. Jaffer, F. A., Tung, C. H., Wykrzykowska, J. J., Ho, N. H., Houng, A. K., Reed, G. L., & Weissleder, R. (2004) *Circulation* 110, 170-6.

21. Siegel, P. M., Ryan, E. D., Cardiff, R. D., Muller W. J. (1999) *EMBO J.*, 18, 2149-64.

22. Suh, T. T., Holmback, K., Jensen, N. J., Daugherty, C. C., Small, K., Simon, D. I., Potter, S., & Degen, J. L. (1995) *Genes Dev.* 9, 2020-2033.

23. Vi, M., Sakai, T., Fassler, R., & Ruoslahti, E. (2003) *Proc. Natl. Acad. Sci. USA*. 100, 11435-11438.

24. Hoffman, R. M. (2005) *Nature Reviews Cancer* 5, 796-806.

25. Laakkonen, P., Akerman, M. E., Biliran, H., Yang, M., Ferrer, F., Karpanen, T., Hoffman, R. M., & Ruoslahti E. (2004) *Proc. Natl. Acad. Sci. USA* 101, 9381-6.

26. Yang, M., Baranov, E., Jiang, P., Sun, F-X., Li, X-M., Li, L., Hasegawa, S., Bouvet, M., Al-Tuwaijri, 26. M., Chishima, T., et al (2000) *Proc. Natl. Acad. Sci.* USA 97, 1206-11.

27. Komatsu, M. & Ruoslahti, E. (2005) *Nat Med.* (2005) 11:1346-1350.

| Sequences | |
|---|---|
| SEQ ID NO: 1 (CLT1): | CGLIIQKNEC |
| SEQ ID NO: 2 (CLT2): | CNAGESSKNC |
| SEQ ID NO: 3: | XGLIIQKNEX |
| SEQ ID NO: 4: | XNAGESSKNX |
| SEQ ID NO: 5: | KAREC |
| SEQ ID NO: 6: | 5'-AATTCCTGCNNKNNKNNKNNK NNKNNKNNKNNKTGCTA-3' (N = any nucleotide, K = guanine or thymine, M = adenine or cytosine) |
| SEQ ID NO: 7 | 3'-GGACGNNMNNMNNMNNMNNMN NMNNMNNMACGATTCGA-5' (N = any nucleotide, K = guanine or thymine, M = adenine or cytosine) |
| SEQ ID NO: 8: | $_D$(KLAKLAK)$_2$ |
| SEQ ID NO: 9: | (KLAKLAK)$_2$ |
| SEQ ID NO: 10: | (KLAKKLA)$_2$ |
| SEQ ID NO: 11: | (KAAKKAA)$_2$ |
| SEQ ID NO: 12: | (KLGKKLG)$_3$ |
| SEQ ID NO: 13: | CALIIQKNEC |
| SEQ ID NO: 14: | CGLILQKNEC |
| SEQ ID NO: 15: | CGLIIQRNEC |
| SEQ ID NO: 16: | CGLIINKNEC |
| SEQ ID NO: 17: | CNAAESSKNC |
| SEQ ID NO: 18: | CNAGESSRNC |
| SEQ ID NO: 19: | CNAGESTKNC |
| SEQ ID NO: 20: | CNAGDSSKNC |
| SEQ ID NO: 21: | AGLIIQKNEA |
| SEQ ID NO: 22: | CNAGESSKNEC |

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps.

Those skilled in the art will recognize, or be able to ascertain using no more than routine experimentation, many equivalents to the specific embodiments of the method and compositions described herein. Such equivalents are intended to be encompassed by the following claims.

The invention claimed is:

1. A conjugate comprising a moiety linked to a peptide comprising the amino acid sequence of SEQ ID NO: 2 or an amino acid sequence at least 90% identical to SEQ ID NO: 2.

2. The conjugate of claim 1, wherein the amino acid sequence of SEQ ID NO: 2 comprises two or three conservative amino acid substitutions.

3. The conjugate of claim 1, wherein the peptide has a length less than 100 residues.

4. The conjugate of claim 1, wherein the peptide has a length of less than 50 residues.

5. The conjugate of claim 1, wherein the peptide has a sequence comprising an amino acid sequence at least 90% identical to SEQ ID NO: 2.

6. The conjugate of claim 1, wherein the peptide consists of the amino acid sequence of SEQ ID NO: 2.

7. The conjugate of claim 1, wherein the peptide is circularized via a disulfide bond.

8. The conjugate of claim 1, wherein the moiety is chosen from a chemotherapeutic agent, a cytotoxic agent, an anti-angiogenic agent, a polypeptide, a nucleic acid molecule, a fluorophore, fluorescein, rhodamine, a radionucleotide, indium-111, technetium-99, carbon-11, and carbon-13.

9. The conjugate of claim 1, wherein the moiety is a therapeutic agent.

10. The conjugate of claim 1, wherein the moiety is a detectable agent.

11. The conjugate of claim 1, wherein the moiety is a virus.

12. The conjugate of claim 1, wherein the moiety is a phage.

13. A method of directing a moiety to a tumor, a site of injury or a site of a blood clot in a subject comprising administering to the subject a conjugate comprising a moiety linked to a peptide comprising the amino acid sequence of SEQ ID NO: 2 or a peptide comprising an amino acid sequence at least 90% identical to SEQ ID NO: 2 thereby directing a moiety to a tumor, a site of injury or a site of a blood clot.

14. The method of claim 13, wherein the amino acid sequence of SEQ ID NO: 2 comprises two or three conservative amino acid substitutions.

15. The method of claim 13, wherein the moiety is directed to tumor stroma in the subject.

16. The method of claim 13, wherein the moiety is directed to a site of injury in a subject.

17. The method of claim 13, wherein the moiety is directed to a site of a blood clot in a subject.

18. The method of claim 13, wherein the moiety is a therapeutic agent.

19. The method of claim 13, wherein the moiety is a detectable agent.

20. The method of claim 13, wherein the peptide is circularized via a disulfide bond.

21. The method of claim 13, wherein the moiety is chosen from a chemotherapeutic agent, a cytotoxic agent, an anti-angiogenic agent, a polypeptide, a nucleic acid molecule, a fluorophore, fluorescein, rhodamine, a radionucleotide, indium-111, technetium-99, carbon-11, and carbon-13.

* * * * *

UNITED STATES PATENT AND TRADEMARK OFFICE
CERTIFICATE OF CORRECTION

| | | |
|---|---|---|
| PATENT NO. | : 9,522,198 B2 | Page 1 of 1 |
| APPLICATION NO. | : 14/331048 | |
| DATED | : December 20, 2016 | |
| INVENTOR(S) | : Erkki Ruoslahti et al. | |

It is certified that error appears in the above-identified patent and that said Letters Patent is hereby corrected as shown below:

In the Specification

In Column 1, Lines 18 through 22, please replace:
"This invention was made with government support under Grant DAMD 17-02-1-0315 from the DoD, Contract NO1-CO-37007 from the NCI, and Grants CA099258 and CA103563 from the NIH. The government has certain rights in the invention."

With:
"This invention was made with government support under DAMD17-02-1-0315 awarded by the US Army Medical Research and Materiel Command, and CA099258, CA103563 and N01 CO037007 awarded by the National Institutes of Health. The government has certain rights in the invention."

Signed and Sealed this
Twenty-second Day of September, 2020

Andrei Iancu
*Director of the United States Patent and Trademark Office*

SEQUENCE LISTING

<160> NUMBER OF SEQ ID NOS: 22

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 1

Cys Gly Leu Ile Ile Gln Lys Asn Glu Cys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 2

Cys Asn Ala Gly Glu Ser Ser Lys Asn Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 1, 10
<223> OTHER INFORMATION: Xaa = any amino acid

<400> SEQUENCE: 3

Xaa Gly Leu Ile Ile Gln Lys Asn Glu Xaa
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 1, 10
<223> OTHER INFORMATION: Xaa = any amino acid

<400> SEQUENCE: 4

Xaa Asn Ala Gly Glu Ser Ser Lys Asn Xaa
1               5                   10

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 5

Lys Ala Arg Glu Cys
1               5

```
<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence; note =
      synthetic construct
<220> FEATURE:
<221> NAME/KEY: misc_feature
<222> LOCATION: 10, 11, 13, 14, 16, 17, 19, 20, 22, 23, 25, 26, 28, 29,
      31, 32
<223> OTHER INFORMATION: n = a, g, c or t (u)

<400> SEQUENCE: 6
aattcctgcn nknnknnknn knnknnknnk nnktgcta                              38

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence; note =
      synthetic construct
<220> FEATURE:
<221> NAME/KEY: misc_feature
<222> LOCATION: 6, 7, 9, 10, 12, 13, 15, 16, 18-22, 24, 25, 27, 28
<223> OTHER INFORMATION: n = a, g, c or t(u)

<400> SEQUENCE: 7
ggacgnnmnn mnmnnmnmnnm nnmnnmnnma cgattcga                             38

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 8

Lys Leu Ala Lys Leu Ala Lys Lys Leu Ala Lys Leu Ala Lys
 1               5                  10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 9

Lys Leu Ala Lys Leu Ala Lys Lys Leu Ala Lys Leu Ala Lys
 1               5                  10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 10

Lys Leu Ala Lys Lys Leu Ala Lys Leu Ala Lys Lys Leu Ala
 1               5                  10
```

```
<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 11

Lys Ala Ala Lys Lys Ala Ala Lys Ala Ala Lys Lys Ala Ala
 1               5                  10

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 12

Lys Leu Gly Lys Lys Leu Gly Lys Leu Gly Lys Lys Leu Gly Lys Leu
 1               5                  10                  15

Gly Lys Lys Leu Gly
            20

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 13

Cys Ala Leu Ile Ile Gln Lys Asn Glu Cys
 1               5                  10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 14

Cys Gly Leu Ile Leu Gln Lys Asn Glu Cys
 1               5                  10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 15

Cys Gly Leu Ile Ile Gln Arg Asn Glu Cys
 1               5                  10

<210> SEQ ID NO 16
<211> LENGTH: 10
<212> TYPE: PRT
<213> ORGANISM: Artificial Sequence
```

```
<220> FEATURE:
<223> OTHER INFORMATION: Description of Artificial Sequence; note =
      synthetic construct

<400> SEQUENCE: 16

Cys Gly Leu Ile Ile Asn Lys Asn Glu Cys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 17

Cys Asn Ala Ala Glu Ser Ser Lys Asn Cys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 18

Cys Asn Ala Gly Glu Ser Ser Arg Asn Cys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 19

Cys Asn Ala Gly Glu Ser Thr Lys Asn Cys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 20

Cys Asn Ala Gly Asp Ser Ser Lys Asn Cys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 21

Ala Gly Leu Ile Ile Gln Lys Asn Glu Ala
1               5                   10
```

```
<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 22

Cys Asn Ala Gly Glu Ser Ser Lys Asn Glu Cys
1               5                   10
```